(12) United States Patent
DeGrado et al.

(10) Patent No.: US 8,258,159 B2
(45) Date of Patent: *Sep. 4, 2012

(54) INHIBITORS OF THE α2β1/GPIA-IIA INTEGRIN

(75) Inventors: William F. DeGrado, Media, PA (US); Joel S. Bennett, Bryn Mawr, PA (US); Seth Elliott Snyder, Bronx, NY (US); Sungwook Choi, San Diego, CA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 444 days.

This patent is subject to a terminal disclaimer.

(21) Appl. No.: 11/916,746

(22) PCT Filed: Jun. 7, 2006

(86) PCT No.: PCT/US2006/022225
§ 371 (c)(1),
(2), (4) Date: Dec. 9, 2008

(87) PCT Pub. No.: WO2006/133338
PCT Pub. Date: Dec. 14, 2006

(65) Prior Publication Data
US 2009/0233968 A1    Sep. 17, 2009

Related U.S. Application Data

(60) Provisional application No. 60/687,972, filed on Jun. 7, 2005.

(51) Int. Cl.
| | | |
|---|---|---|
| *A01N 43/40* | (2006.01) | |
| *A01N 43/36* | (2006.01) | |
| *A61K 31/445* | (2006.01) | |
| *A61K 31/40* | (2006.01) | |

(52) U.S. Cl. ........................................ 514/327; 514/423
(58) Field of Classification Search ........................ None
See application file for complete search history.

(56) References Cited

U.S. PATENT DOCUMENTS

| | | | |
|---|---|---|---|
| 6,096,707 A | 8/2000 | Heino et al. | |
| 6,369,034 B1 | 4/2002 | Doherty et al. | |
| 6,423,688 B1 | 7/2002 | Thorsett et al. | |
| 6,645,939 B1 | 11/2003 | Durette et al. | |
| 6,734,311 B2 | 5/2004 | Hagmann et al. | |
| 6,900,179 B2 | 5/2005 | Thorsett et al. | |
| 6,943,180 B2 | 9/2005 | Doherty et al. | |
| 7,910,609 B2 * | 3/2011 | DeGrado et al. | 514/327 |
| 2003/0100585 A1 | 5/2003 | DuPlantier et al. | |
| 2004/0072850 A1 | 4/2004 | Knegtel et al. | |
| 2009/0197861 A1 * | 8/2009 | DeGrado et al. | 514/210.17 |
| 2010/0179119 A1 * | 7/2010 | DeGrado et al. | 514/210.17 |

FOREIGN PATENT DOCUMENTS

| | | | |
|---|---|---|---|
| JP | 61176599 A * | 8/1986 | |
| JP | 05140196 A * | 6/1993 | |
| WO | WO 03/008380 A1 | 1/2003 | |
| WO | WO 2006/133338 A1 | 12/2006 | |
| WO | WO 2007/027742 A2 | 3/2007 | |

OTHER PUBLICATIONS

Ettmayer et al. Lessons Learned from Marketed and Investigational Prodrugs. J Med Chem 2004, vol. 47, No. 10, pp. 2393-2404.*
Han et al. Targeted Prodrug Design to Optimize Drug Delivery. AAPS Pharmsci 2000. vol. 2, No. 1, article 6, p. 1.*
Testa. Prodrug research: futile or fertile? biochem Pharmacol. 2004, vol. 68, pp. 2097-2106.*
Vippagunta et al. Crystalline solids. Adv. Drug Delivery Reviews. 2001, vol. 48, pp. 3-26.*
Baronas-Lowell D, Lauer-Fields JL, Borgia JA, Sferrazza GF, Al-Ghoul M, Minond D, Fields GB. Differential Modulation of Human Melanoma Cell Metalloproteinase Expression by Alpha2Beta1 Integrin and CD44 Triple-Helical Ligands Derived from Type IV Collagen. J Biol Chem. 279(42), 43503-13, 2004.
Bellavite, P. A., G.; Guzzo, P.; Arigliano, P.; Chirumbolo, S.; Manzato, F.; Santonastaso, C. A Colorimetric Method for the Measure of Platelet Adhesion in Microtiter Plates. Anal. Biochem. 1994, 216, 444-450.
Bennett, J. S. a. V., G. Exposure of platelet fibrinogen receptors by ADP and epinephrine. J. Clin. Invest. 1979, 64, 1393-1401.
Bennett, J. S. C., C.; Vilaire, G.; Mousa, S. A.; DeGrado, W. F. Agonist-Activated alphavbeta3 on Platelets and Lymphocytes Binds to the Matrix Protein Osteopontin. J. Biol. Chem. 1997, 272, 8137-8140.
Bennett, J. S. Structure and function of the platelet integrin alphaIIb-beta3. J. Clin. Invest. 2005, 115, 3363-3369.
Chen et al, "EvidenceThat Ligand and Metal Ion Binding to Integrin a4b1 Are Regulated through a Coupled Equilibrium," The Journal of Biological Chemistry, 276(39), 36520-36529, 2001.
Chen H, Kahn ML. Reciprocal signaling by integrin and nonintegrin receptors during collagen activation of platelets. Mol Cell Biol. 23(14):4764-77, 2003.
Choi, S. V., G.; Marcinkiewicz, C.; Winkler, J. D.; Bennett, J. S.; DeGrado, W. F. . Small Molecule Inhibitors of Integrin alpha2beta1. J. Med. Chem. 2007, 50, 5457-5462. Connors, W. L. J., J.; White, D. J.; Puranen, J. S.; Kankaanpaa, P.; Upla, P.; Tulle, M.; Johnson, M. S.; Heino, J. Two synergistic activation mechanisms of integrin alpha2beta1 integrin-mediated collagen binding. J. Biol. Chem. 2007, 282, 14675-14683.
DeWood, M. A. S., J.; Notske, R.; Mouser, L. T.; Burroughs, R.; Golden, M. S.; Lang, K. T. . Prevalence of Total Coronary Occlusion During the Early Hours of Transmural Myocardial Infarction. N. Eng. J. Med. 1980, 303, 897-902.
Emsley J, Knight CG, Farndale RW, Barnes MJ, Liddington RC. Structural Basis of Collagen Recognition by Integrin Alpha2Beta1. Cell. 101(1), 47-56, 2000.
Emsley, J. K., S. L.; Bergelson, J. M.; Liddington, R. C. Crystal Structure of the I Domain from Integrin alpha2beta1. J. Biol. Chem. 1997, 273, 28512-28517.
Falk, E, Shah, P.K. & Fuster, V. Coronary Plaque Disruption. Circulation 92, 657-671 (1995).
Feire AL, Koss H, Compton T. Cellular Integrins Function as Entry Receptors for Human Cytomegalovirus via a Highly Conserved Disintegrin-Like Domain. Proc Natl Aced Sci U S A. 101(43), 15470-5, 2004.

(Continued)

*Primary Examiner* — Marcela M Cordero Garcia
(74) *Attorney, Agent, or Firm* — Woodcock Washburn, LLP

(57) ABSTRACT

Novel compounds inhibiting the integrin α2β1/GPIa-IIa receptor are disclosed. Also disclosed are pharmaceutical compositions containing the compounds, as well as methods of their therapeutic use. The compounds disclosed are useful, inter alia, as inhibitors of integrin α2β1/GPIa-IIa-mediated activity.

33 Claims, No Drawings

OTHER PUBLICATIONS

Ferarra, N. The Role of Vascular Endothelial Growth Factor in Pathological Angiogenesis. Breast Cancer Res Treat. 36(2), 127-37, 1995.

Folkman J. Angiogenesis in Cancer, Vascular, Rheumatoid and Other Disease. Nat Med. 1(1), 27-31, 1995.

Furihata, K. N., D. J.; Kunicki, T. J. Influence of platelet collagen receptor polymorphisms on risk for arterial thrombosis. Arch. Pathol. Lab. Med. 2002, 126, 305-309.

Fuster, V., Badimon, L., Badimon, J.J. & Chesebro, J.H. The Pathogenesis of Coronary Artery Disease and the Acute Coronary Syndromes (1). N. Engl. J. Med. 326, 242-250, 1992.

Graham KL, Halasz P, Tan Y, Newish MJ, Takada Y, Mackow ER, Robinson MK, Coulson BS. Integrin-using rotaviruses bind alpha2beta1 integrin alpha2 I domain via VP4 DGE sequence and recognize alphaXbeta2 and alphaVbeta3 by using VP7 during cell entry. J Virol. 77(18), 9969-78, 2003.

Hagmann, W.K., The discovery and potential of N-sulfonylated dipeptide VLA-4 antagonists. Curr. Top Med. Chem., 2004, 4(14), 1461-1471.

Han J, Jenq W, Kefalides NA. Integrin Alpha2Beta1 Recognizes Laminin-2 and Induces C-erb B2 Tyrosine Phosphorylation in Metastatic Human Melanoma Cells. Connect Tissue Res. 40(4), 283-93, 1999.

Handa, M., ; Watanabe, K.; Kawai, Y.; Kamata, T.; Koyama, T.; Nagai, H.; Ikeda, Y. Platelet unresponsiveness to collagen: involvement of glycoprotein Ia-IIa (alpha2beta1 integrin) deficiency associated with a myeloproliferative disorder. Thromb. Haemost. 1995, 73, 521-528.

He L, Pappan LK, Grenache DG, Li Z, Tollefsen DM, Santoro SA, Zutter MM. The contributions of the alpha 2 beta 1 integrin to vascular thrombosis in vivo. Blood. 102(10):3652-7, 2003.

Holtkotter, O. N., B.; Smyth, N.; Muller, W.; Hafner, M.; Schulte, V.; Krieg, T.; Eckes, B. Integrin alpha2-deficient mice develop normally, are fertile, but display partially defective platelet interaction with collagen. J. Biol. Chem. 2002, 277, 10789-10794.

Huryn, D.M. et al., The identification and optimization of orally efficacious, small molecule VLA-4 antagonists. Curr. Top. Med. Chem., 2004, 4(14), 1473-1484.

Huryn, D.M. et al., Synthesis, characterization and evaluation of pro-drugs of VLA-4 antagonists. Bioorg. Med. Chem Lett., Apr. 5, 2004, 14(7), 1651-1654 Erratum in: Bioorg Med Chem Lett. Nov. 1, 2004;14(21):5449.

Hynes RO. Integrins: bidirectional, allosteric signaling machines. Cell. 110(6):673-87. Review, 2002.

Inoue, O. et al., Integrin alpha2beta1 mediates outside-in regulation of platelet spreading on collagen through activation of Src Kinases and PLCgamma2. J. Cell Biol. 160(5): 769-80 (2003).

Jackson SP and Schoenwaelder SM. Antiplatelet Therapy: In Search of the 'Magic Bullet'. Nat. Rev. Drug. Discov. 2(10), 775-89, 2003.

Jung SM, Moroi M. Platelets interact with soluble and insoluble collagens through characteristically different reactions. J Biol Chem. 273(24):14827-37, 1998.

Jung, S. M. a. M., M. Signal-transducing mechanisms involved in activation of the platelet collagen receptor integrin alpha2beta1. J. Biol. Chem. 2000, 275, 8016-8026.

Kamenecka TM, Lanza T Jr, de Laszlo SE, Li B, McCauley ED, Van Riper G, Egger LA, Kidambi U, Mumford RA, Tong S, MacCoss M, Schmidt JA, Hagmann WK. N-aryl-prolyl-dipeptides as potent antagonists of VLA-4. Bioorg Med Chem Lett. Aug. 19, 2002;12(16):2205-8.

Kehrel, B. B., L.; Kokott, R.; Mesters, R.; Stenzinger, W.; Clemetson, K. J.; van der Loo, J. Deficiency of intact thrombospondin and membrane glycoprotein Ia in platelets with defective collagen-induced aggregation and spontaneous loss of disorder. Blood 1988, 71, 1074-1078.

Knight, C.G. et al., The collagen-binding A-domains of integrins alpha(1)beta(1) and alpha(2)beta(1) recognize the same specific amino acid sequence, GFOGER, in native (triple-helical) collagens. J. Biol. Chem., 2000, 275, 35-40.

Knutson JR, Iida J, Fields GB, McCarthy JB. CD44/Chondroitin Sulfate Proteoglycan and Alpha 2 Beta 1 Integrin Mediate Human Melanoma Cell Migration on Type IV Collagen and Invasion of Basement Membranes. Mol Biol Cell. 7(3), 383-96, 1996.

Koo, G.C. et al., A small molecule very late antigen-4 antagonist can inhibit ovalbumin-induced lung inflammation. Am. J. Respir. Crit. Care Med., May 15, 2003, 167(10), 1400-1409.

Kritzik M, Savage B, Nugent DJ, Santoso S, Ruggeri ZM, Kunicki TJ. Nucleotide polymorphisms in the alpha2 gene define multiple alleles that are associated with differences in platelet alpha2 beta1 density. Blood. 92(7):2382-8 (1998).

Kufrin, D. et al., "Antithrombotic thrombocytes: ectopic expression of urokinase-type plasminogen activator in platelets," Blood, 2003, 102(3), 926-933.

Kuijpers, M.J. et al., Complementary roles of glycoprotein VI and alpha2beta1 integrin in collagen-induced thrombus formation in flowing whole blood ex vivo. FASEB J., 2003, 17(6), 685-687.

Kumar R. Aseptic meningitis: Diagnosis and management. Indian J Pediatr. 72(1), 57-63, 2005.

Kunicki, T. J. O., R.; Annis, D.; Honda, Y. Variability of integrin alpha2beta1 activity on human platelets. Blood 1993, 82, 2693-2703.

Leone et al., "An Assessment of the Mechanistic Differences Between Two Integrin a4b1 Inhibitors, the Monoclonal Antibody TA-2 and the Small Molecule BIO5192, in Rat Experimental Autoimmune Encephalomyelitis," The Journal of Pharmacology and Experimental Therapeutics, 305(3), 1150-1162, 2003.

Lin LS, Lanza TJ Jr, Castonguay LA, Kamenecka T, McCauley E, Van Riper G, Egger LA, Mumford RA, Tong X, MacCoss M, Schmidt JA, Hagmann WK. Bioisosteric replacement of anilide with benzoxazole: potent and orally bioavailable antagonists of VLA-4. Bioorg Med Chem Lett. May 3, 2004;14(9):2331-4.

Londrigan SL, Graham KL, Takada Y, Halasz P, Coulson BS. Monkey rotavirus binding to alpha2beta1 integrin requires the alpha2 I domain and is facilitated by the homologous beta1 subunit. J Virol. 77(17), 9486-501, 2003.

Lu, C. S., M.; Zang, Q.; Takagi, J.; Springer, T. A. Locking in Alternate Conformations of the Integrin aLb2 I Domain with Disulfide Bonds Reveals Functional Relationships Among Integrin Domains. PNAS 2001, 98, 2393-2398.

Luo, B.-H. C., C. V.; Springer, T. A. Structural basis of integrin signaling and regulation. Annu. Rev. Immunol. 2007, 25, 619-647.

Nieswandt B, Brakebusch C, Bergmeier W, Schulte V, Bouvard D, Mokhtari-Nejad R, Lindhout T, Heemskerk JW, Zirngibl H, Fassler R. Glycoprotein VI But Not Alpha2Beta1 Integrin is Essential for Platelet Interaction With Collagen. EMBO J. 20(9), 2120-30, 2001.

Nieswandt B, et al. (2001); Ruggeri ZM. Platelets in Atherothrombosis. Nat Med. 8(11), 1227-34, 2002.

Nieswandt B, Watson SP. Platelet-Collagen Interaction: Is GPVI the Central Receptor? Blood. 102(2), 449-6, 2003.

Nieuwenhuis HK, Sakariassen KS, Houdijk WP, Nievelstein PF, Sixma JJ. Deficiency of Platelet Membrane Glycoprotein Ia Associated With a Decreased Platelet Adhesion to Subendothelium: A Defect in Platelet Spreading. Blood. 68(3), 692-5, 1986.

Nieuwenhuis, H. K. A., J. W. N.; Houdijk, W. P. M.; Sixma, J. J. Human blood platelets showing no response to collagen fail to express surface glycoprotein Ia. Nature 1985, 318, 470-472.

Onley DJ, Knight CG, Tuckwell DS, Barnes MJ, Farndale RW. Micromolar Ca2+ concentrations are essential for Mg2+-dependent binding of collagen by the integrin alpha 2beta 1 in human platelets. J Biol Chem. 275(32):24560-4, 2000.

Pepinsky RB, Mumford RA, Chen LL, Leone D, Amo SE, Riper GV, Whitty A, Dolinski B, Lobb RR, Dean DC, Chang LL, Raab CE, Si Q, Hagmann WK, Lingham RB. Comparative assessment of the ligand and metal ion binding properties of integrins alpha9beta1 and alpha4beta1. Biochemistry. Jun. 4, 2002;41(22):7125-41.

Rosamond, W. F., K.; Furie, K.; Go, A.; Greenlund, K.; Haase, K.; Hailpern, S. M.; Ho, M.; Howard, V.; Kissela, B.; Kittner, S.; Lloyd-Jones, D.; McDermott, M.; Meigs, J.; Moy, C.; Nichol, G.; O'Donnell, C.; Roger, V.; Sorlie, P.; Steinberger, J.; Thom, T.; Wilson, M; Hong, Y. . Heart disease and stroke statistics 2008 update. A report from the American Heart Association Circulation Prepublished online: Dec. 17, 2007, DOI: 10.1161/CIRCULATIONAHA.107.187998.

Saelman, E. U. M. N., H. K.; Hese, K. M.; de Groot, P. G.; Heijnen, H. F. G.; Sage, E. H.; Williams, S.; McKeown, L.; Gralnick, H. R.; Sixma, J. J. Platelet Adhesion to Collagen Types I through VIII Under Conditions of Stasis and Flow is Mediated by GPIa/IIIa (alpha2beta1-Integrin). Blood 1994, 83, 1244-1250.
Santoro SA. Identification of a 160,000 Dalton Platelet Membrane Protein That Mediates the Initial Divalent Cation-dependent Adhesion of Platelets to Collagen. Cell. 46(6), 913-20, 1986.
Santoro, S. A. Platelet Surface Collagen Polymorphisms: Variable Receptor Expression and Thrombotic/Hemorrhagic Risk. Blood 1999, 93, 3575-3577.
Savage B, Ginsberg MH, Ruggeri ZM. Influence of Fibrillar Collagen Structure on the Mechanisms of Platelet Thrombus Formation Under Flow. Blood. 94(8), 2704-15, 1999.
Senger DR, Perruzzi CA, Streit M, Koteliansky VE, de Fougerolles AR, Detmar M. The Alpha(1)Beta(1) and Alpha(2)Beta(1) Integrins Provide Critical Support for Vascular Endothelial Growth Factor Signaling, Endothelial Cell Migration, and Tumor Angiogenesis. Am J Pathol. 160(1), 195-204, 2002.
Senger DR, Van de Water L, Brown LF, Nagy JA, Yeo KT, Yeo TK, Berse B, Jackman RW, Dvorak AM, Dvorak HF. Vascular Permeability Factor (VPF, VEGF) in Tumor Biology. Cancer Metastasis Rev. 12(3-4), 303-24, 1993.
Shattil, S. J. a. N., P. J. Integrins: Dynamic Scaffolds for Adhesion and Signaling in Platelets. Blood 2004, 104, 1606-1615.
Shimaoka M, Sales A, Yang W, Weitz-Schmidt G, Springer TA. Small molecule integrin antagonists that bind to the beta2 subunit I-like domain and activate signals in one direction and block them in the other. Immunity. 19(3):391-402, 2002.
Siljander PR, Munnix IC, Smethurst PA, Deckmyn H, Lindhout T, Ouwehand WH, Farndale RW, Heemskerk JW. Platelet receptor interplay regulates collagen-induced thrombus formation in flowing human blood. Blood. 103(4):1333-41, 2004.
Stasiak M, Mehlin C, Boni E, Vaisar T, Little T, Kim HO, Qabar M. Sulphonamide-based small molecule VLA-4 antagonists. Bioorg Med Chem Lett. Nov. 3, 2003;13(21):3875-8.
Sweeney SM, DiLullo G, Slater SJ, Martinez J, Iozzo RV, Lauer-Fields JL, Fields GB, San Antonio JD. Angiogenesis in Collagen I Requires Alpha2Beta1 Ligation of a GFP*GER Sequence and Possibly p38 MAPK Activation and Focal Adhesion Disassembly. J Biol Chem. 278(33), 30516-24, 2003.
Takagi, J. P., B. M.; Walz, T.; Springer, T. A. Global conformational rearrangements in integrin extracellular domains in outside-in and inside-out signaling. Cell 2002, 110, 599-611.
Tam, S. H. S., P. M.; Jordan, R. E.; Nakada, M. T. Abciximab (ReoPro, chimeric 7E3 Fab) demonstrates equivalent affinity and functional blockade of glycoprotein IIb/IIIa and alphavbeta3 integrins. Circulation 1998, 98, 1085-1091.
Triantafilou K & Triantafilou M. A biochemical approach reveals cell-surface molecules utilised by Picornaviridae: Human Parechovirus 1 and Echovirus 1. J Cell Biochem. 80(3), 373-81, 2001.
Tuckwell D, Calderwood DA, Green LJ, Humphries MJ. Integrin alpha 2 I-domain is a binding site for collagens. J Cell Sci. 108(Pt 4):1629-37, 1995.
Watson, S. P. a. G., J. Collagen receptor signaling in platelets: extending the role of the ITAM. Immunol. Today 1998, 19, 260-264.
Welzenbach, K. H., U.; Weitz-Schmidt, G. Small molecule inhibitors induce conformational changes in the I-domain and the I-like domain of lymphocyte function-associated antigen-1. J. Biol. Chem. 2002, 277, 10590-10598.
White, T. C. B., M. A.; Robinson, D. K.; Yin, H.; DeGrado, W. F.; Hanson, S. R.; McCarty, O. J. . The Leech Product Saratin is a Potent Inhibitor of Platelet Integrin alpha2beta1 and von Willebrand Factor Binding to Collagen. FEBS J. 2007, 274, 1481-1491.
Yang C, Zeisberg M, Lively JC, Nyberg P, Afdhal N, Kalluri R. Integrin Alpha1Beta1 and Alpha2Beta1 Are the Key Regulators of Hepatocarcinoma Cell Invasion Across the Fibrotic Matrix Microenvironment. Cancer Res. 63(23), 8312-7, 2003.
U.S. Appl. No. 12/237,015 by William F. DeGrado et al., filed Sep. 24, 2008.
U.S. Appl. No. 61/099,747 by William F. DeGrado, et al., filed Sep. 24, 2008.
U.S. Appl. No. 60/687,972 by William F. DeGrado, et al., filed Jun. 7, 2005.
U.S. Appl. No. 60/712,775 by Seth E. Snyder, et al., filed Aug. 31, 2005.

* cited by examiner

INHIBITORS OF THE α2β1/GPIA-IIA INTEGRIN

CROSS-REFERENCE TO RELATED APPLICATIONS

This application is the National Stage of International Application No. PCT/US2006/022225 filed Jun. 7, 2006, which claims the benefit of U.S. Provisional Application No. 60/687,972, filed Jun. 7, 2005, the disclosure of which is incorporated herein by reference in its entirety.

GOVERNMENT RIGHTS

The United States Government may have rights in the invention described herein, which was made in part with funding from the U.S. National Institutes of Health (NIH), Grant Nos. PO1HL40387-011 (J. Bennett) May 5, 2003-Mar. 31, 2008 and P50 HL54500 (J. Bennett) Mar. 15, 2001-Jan. 31, 2006.

FIELD OF THE INVENTION

The present invention relates to small molecule inhibitors of the α2β1/GPIa-IIa integrin, as well as methods of production, use, and therapeutic administration thereof.

BACKGROUND OF THE INVENTION

Recruitment, adhesion, and aggregation of platelets at sites of vascular injury are critical to generation of beneficial blood clotting events. However, excessive accumulation of platelets, e.g., at sites of ruptured atheriosclerotic plaques, can give rise to the development of acute coronary syndromes, stroke, ischaemic complications of peripheral vascular disease, and other disease states. Fuster, V., Badimon, L., Badimon, J. J. & Chesebro, J. H. *The Pathogenesis of Coronary Artery Disease and the Acute Coronary Syndromes* (1). *N. Engl. J. Med.* 326, 242-250 (1992); Falk, E, Shah, P. K. & Fuster, V *Coronary Plaque Disruption. Circulation* 92, 657-671 (1995). Promise for enhanced clinical management of such vascular diseases has arisen in recent years with progress in understanding of the mechanisms underlying the formation of arterial plaque and thrombosis and of the criticality of the role of platelet activity in the development of cardiovascular disease.

Tempered by the understanding that antithrombotic treatment should be effective and yet avoid undermining hemostasis, clinicians of cardiovascular disease prevention and treatment have depended on mild therapeutic agents like aspirin and clopidogrel for widespread application. There are a variety of other antithrombotic drugs, including coumadin and abciximab (ReoPro®), ticlopidine, and others, but there remains an urgent need for newer and safer antithrombotics, to address stroke, deep vein thrombosis (DVT), myocardial infarction, coronary artery disease, cerebrovascular disease, peripheral arterial disease, diabetes mellitus, atrial fibrillation, congestive heart failure, and other vascular disorders. Jackson S P and Schoenwaelder S M. *Antiplatelet Therapy: In Search of the 'Magic Bullet'. Nat. Rev. Drug. Discov.* 2 (10), 775-89 (2003). *Review.* More versatile and effective and yet selective and safe therapeutic agents are currently the object of extensive research worldwide, especially in light of the increasing prevalence of cardiovascular disease both due to changes in diet and lifestyle and in view of the aging of the population. Special emphasis has been placed on the issue of improving efficacy without compromising safety, since all forms of presently available antithrombotic therapies cannot be administered at potent doses without producing negative physiological conditions, primarily bleeding events.

Upon vessel injury and attendant removal or damage of the protective endothelial lining, platelets encounter a diverse set of proteins from the connective tissue of the vessel wall. These include collagen and von Willebrand factor (vWf). Platelet adhesion to these proteins and subsequent activation is mediated by a multitude of platelet receptors. Adhesion of platelets to the extracellular matrix triggers a series of signaling events that ultimately result in formation of a hemostatic plug known as a thrombus. Recent findings provide strong evidence that immediately following vessel rupture, the platelet receptor GPVI binds loosely to exposed collagen, which is alone insufficient to induce stable platelet adhesion, but which triggers a tyrosine kinase-based signaling pathway that results in major conformational changes and attendant activation in specific receptors, including integrin α2β1. Emsley J, Knight C G, Farndale R W, Barnes M J, Liddington R C. *Structural Basis of Collagen Recognition by Integrin Alpha2Beta1. Cell.* 101 (1), 47-56 (2000).

Integrin α2β1, also known as platelet GPIa-IIa, was the first collagen receptor to be identified on platelets. Nieuwenhuis H K, Akkerman J W, Houdijk W P, Sixma J J. *Human Blood Platelets Showing No Response to Collagen Fail to Express Surface Glycoprotein Ia. Nature.* 318 (6045), 470-2 (1985); Santoro S A. *Identification of a 160,000 Dalton Platelet Membrane Protein That Mediates the Initial Divalent Cation-dependent Adhesion of Platelets to Collagen. Cell.* 46 (6), 913-20 (1986). Similar to other members of the integrin family, α2β1 inks the cytoskeleton of the cell with the extracellular matrix. Hynes R O. *Integrins: bidirectional, allosteric signaling machines. Cell.* 110 (6):673-87. *Review* (2002). Besides playing an essential role in adhesion to the extracellular matrix, integrins are indispensable for cellular signaling. All integrins are heterodimers, consisting of an α subunit and a β subunit. About half of the known mammalian integrins, including α2β1, have an I-domain inserted into the α subunit (Hynes, 2002). In these cases, the I-domain is responsible for binding of the integrin to its natural ligand(s). A specific amino acid sequence in collagen, GFOGER (O=hydroxyproline), promotes stable binding to the I-domain of α2β1. Onley D J, Knight C G, Tuckwell D S, Barnes M J, Farndale R W. *Micromolar Ca2+ concentrations are essential for Mg2+-dependent binding of collagen by the integrin alpha 2beta 1 in human platelets. J Biol. Chem.* 275 (32):24560-4 (2000). Binding occurs in a cation dependent manner, supported by either magnesium or manganese Tuckwell D, Calderwood D A, Green L J, Humphries M J. *Integrin alpha 2 I-domain is a binding site for collagens. J Cell Sci.* 108 (*Pt* 4):1629-37 (1995). A crystal structure of a complex between the I-domain of α2β1 and a triple helical peptide containing the GFOGER sequence has been solved. Emsley J, Knight C G, Farndale R W, Barnes M J, Liddington R C. *Structural basis of collagen recognition by integrin alpha2beta1. Cell.* 101 (1), 47-56 (2000). A glutamic acid (E) from the middle strand of the triple helix coordinates to metal-ion dependent adhesion site (MIDAS) while other residues of the GFOGER motif from the middle and trailing strands interact with complementary sites on the I-domain surface.

Importantly, integrin α2β1 has multiple states of activation which can be regulated from inside or outside of the cell. Hynes R O. *Integrins: bidirectional, allosteric signaling machines. Cell.* 110 (6):673-87. *Review* (2002). For instance, signaling through the platelet receptor GPVI impinges upon the cytoplasmic domain of α2β1, which results in a dramatic conformational change that eventually propagates along the α2β1 integrin, ultimately affecting the I-domain at the integrin's head. Integrin activation is induced by several other platelet agonists, including ADP and thrombin. Jung S M, Moroi M. *Platelets interact with soluble and insoluble collagens through characteristically different reactions. J. Biol Chem.* 273 (24):14827-37 (1998). The activated integrin can than bind tightly to collagen. This adhesion can potentially be blocked with either a direct competitor of the collagen/I-domain interaction or with an allosteric regulator, the latter of which precludes activation of the I domain. Two types of small-molecule inhibitors have been developed for a related integrin, αLβ2. Shimaoka M, Salas A, Yang W Weitz-Schmidt G, Springer T A. *Small molecule integrin antagonists that bind to the beta2 subunit I-like domain and activate signals in one direction and block them in the other. Immunity.* 19 (3):391-402 (2002). The first binds to the I-domain of αLβ2 at a distant site from the MIDAS, blocking activation of its I domain and subsequent binding to ICAM-1. The second binds to the I-like domain of the β subunit, which is located directly beneath the I domain. A direct competitive inhibitor of an I-domain/ligand interaction has not yet been reported.

Despite the fact that α2β1 integrin was discovered more than 15 years ago, its precise role in platelet adhesion and aggregation remains controversial. This is partially due to the overlapping functions of α2β1 and GPVI. Chen H, Kahn M L. *Reciprocal signaling by integrin and nonintegrin receptors during collagen activation of platelets. Mol Cell Biol.* 23 (14):4764-77 (2003). Integrin α2β1 is essential for platelet adhesion and activation on monomeric type I collagen; it has been demonstrated through platelet analysis that adhesion and thrombus growth on pepsin-solubilized type I collagen under low and high shear flow conditions is absolutely dependent on functional α2β1. Savage B, Ginsberg M H, Ruggeri Z M. *Influence of Fibrillar Collagen Structure on the Mechanisms of Platelet Thrombus Formation Under Flow. Blood.* 94 (8), 2704-15 (1999); Nieswandt B, Brakebusch C, Bergmeier W, Schulte V, Bouvard D, Mokhtari-Nejad R, Lindhout T, Heemskerk J W, Zirngibl H, Fassler R. *Glycoprotein VI But Not Alpha2Beta1 Integrin is Essential For Platelet Interaction With Collagen. EMBO J.* 20 (9), 2120-30 (2001). However, on the more physiologically relevant insoluble collagen (fibrillar collagen), α2β1 integrin may be dispensable, at least in the context of hemostasis. Nieswandt B, Watson S P. *Platelet-Collagen Interaction: Is GPVI the Central Receptor? Blood.* 102 (2), 449-6 (2003). Review. For instance, fibrillar collagen-induced aggregation of β1-null mouse platelets is not reduced, despite a slight time delay. Nieswandt B, Brakebusch C, Bergmeier W, Schulte V, Bouvard D, Mokhtari-Nejad R, Lindhout T, Heemskerk J W, Zirngibl H, Fassler R. *Glycoprotein VI But Not Alpha2Beta1 Integrin is Essential For Platelet Interaction With Collagen. EMBO J.* 20 (9), 2120-30 (2001). Furthermore, the β1-null platelets adhere normally to fibrillar collagen under static conditions. Nonetheless, it has been established that adhesion under physiological conditions of blood flow requires a functional α2β1 integrin. Siljander P R, Munnix I C, Smethurst P A, Deckmyn H, Lindhout T, Ouwehand W H, Farndale R W, Heemskerk J W *Platelet receptor interplay regulates collagen-induced thrombus formation in flowing human blood. Blood.* 103 (4): 1333-41 (2004).

Studies of platelets derived from two individuals with an integrin α2β1 deficiency have demonstrated a defect in adhesion and spreading on the subendothelium. Nieswandt B, et al. (2001); Ruggeri Z M. *Platelets In Atherothrombosis. Nat. Med.* 8 (11), 1227-34 (2002). Review. Indeed, these patients exhibit only modest degree of defect in hemostasis, manifested as only minor bleeding complications. Nieuwenhuis H K, et al., *Nature.* 318 (6045), 470-2 (1985); Nieuwenhuis H K, Sakariassen K S, Houdijk W P, Nievelstein P F, Sixma J J. *Deficiency of Platelet Membrane Glycoprotein Ia Associated With a Decreased Platelet Adhesion to Subendothelium: A Defect in Platelet Spreading. Blood.* 68 (3), 692-5 (1986). This has important implications for the search for antithrombotic therapies with favorable safety profiles. It suggests that antagonism of α2β1 integrin will have a beneficially mild antithrombotic effect; increasing amount of evidence indeed suggests that α2β1 may have a greater role in pathological thrombosis relative to normal hemostasis. This observation may reflect the fact that an increased amount of collagen accumulates in diseased blood vessels. For instance, the extracellular matrix around an atheroslerotic lesion is heavily enriched in collagens. Nieswandt B, et al., (2003). Besides providing an adhesive support for platelets, collagen sends potent prothrombotic signals into the cell through interaction with its platelet receptors. Overexpression of α2β1 integrin has been linked to cardiovascular disease in humans. Kritzik M, Savage B, Nugent D J, Santoso S, Ruggeri Z M, Kunicki T J *Nucleotide polymorphisms in the alpha2 gene define multiple alleles that are associated with differences in platelet alpha2 beta1 density. Blood.* 92 (7):2382-8 (1998). Furthermore, recent in vivo data indicates that α2β1-deficient mice have delayed thrombus formation following carotid artery injury. He L, Pappan L K, Grenache D G, Li Z Tollefsen D M, Santoro S A, Zutter M M. *The contributions of the alpha 2 beta 1 integrin to vascular thrombosis in vivo. Blood.* 102 (10):3652-7 (2003). These data reveal a critical role for α2β1 in thrombosis. Hence, the α2β1 integrin is an important pharmacological target for cardiovascular diseases, and the resulting treatment is expected to be well-tolerated and provide long-term antithrombotic protection.

Equally significant, the α2β1 integrin may be a target for cancer, several types of viral infections, and other pathologies. Overexpression of α2β1 in various types of cancer cells, particularly in human melanoma cells and hepatocellular carcinomas, has been linked to tumor metastasis. Han J. Jenq W, Kefalides N A. *Integrin Alpha2Beta1 Recognizes Laminin-2 and Induces C-erb B2 Tyrosine Phosphorylation in Metastatic Human Melanoma Cells. Connect Tissue Res.* 40 (4), 283-93 (1999). Yang C, Zeisberg M, Lively J C, Nyberg P, Afdhal N, Kalluri R. *Integrin Alpha1Beta1 and Alpha2Beta1 Are the Key Regulators of Hepatocarcinoma Cell Invasion Across the Fibrotic Matrix Microenvironment. Cancer Res.* 63 (23), 8312-7 (2003). The α2β1 integrin is known to be the primary melanoma cell adhesion molecule for type IV collagen, indicating a key role for that integrin in pathological metastasis Knutson J R, Iida J, Fields G B, McCarthy J B. *CD44/Chondroitin Sulfate Proteoglycan and Alpha 2 Beta 1 Integrin Mediate Human Melanoma Cell Migration on Type IV Collagen and Invasion of Basement Membranes. Mol Biol Cell.* 7 (3), 383-96 (1996). Ligand binding by the α2β1 integrin triggers a series of intracellular signaling events that ultimately result in the release of cytokines and proteases, both of which are beneficial for tumor cell progression. Baronas-Lowell D, Lauer-Fields J L, Borgia J A, Sferrazza G F, Al-Ghoul M, Minond D, Fields G B. *Differential Modulation of Human Melanoma Cell Metalloproteinase Expression by Alpha2Beta1 Integrin and CD44 Triple-Helical Ligands Derived from Type IV Collagen. J Biol Chem.* 279 (42), 43503-13 (2004). Furthermore, antagonism of the α2β1 integrin suppresses angiogenesis. Senger D R, Perruzzi C A, Streit M, Koteliansky V E, de Fougerolles A R, Detmar M. *The Alpha(1)Beta(1) and Alpha(2)Beta(1) Integrins Provide Critical Support For Vascular Endothelial Growth Factor Signaling, Endothelial Cell Migration, and Tumor Angiogenesis. Am J Pathol.* 160 (1), 195-204 (2002). This has profound implications since angiogenesis is involved in growth and metastasis of solid tumors, rheumatoid arthritis, diabetic retinopathy, and a variety of other important disease states. Folkman J. *Angiogenesis in Cancer, Vascular, Rheumatoid and Other Disease. Nat. Med.* 1 (1), 27-31 (1995). Review; Senger D R, Van de Water L, Brown L F, Nagy J A, Yeo K T, Yeo T K, Berse B, Jackman R W, Dvorak A M, Dvorak H F. *Vascular Permeability Factor (VPF, VEGF) in Tumor Biology. Cancer Metastasis Rev.* 12 (3-4), 303-24 (1993). Review; Ferarra, N. *The Role of Vascular Endothelial Growth Factor in Pathological Angiogenesis. Breast Cancer Res Treat.* 36 (2), 127-37 (1995). Review. Specific blocking of α2β1 function halts capillary morphogenesis, the essential antecedent to angiogenesis, whereas blocking of related integrin dimers or monomer subunits does not similarly arrest morphogenesis. Sweeney S M, DiLullo G, Slater S J, Martinez J, Iozzo R V, Lauer-Fields J L, Fields G B, San Antonio J D. *Angiogenesis in Collagen I Requires Alpha2Beta1 Ligation of a GFP\*GER Sequence and Possibly p38 MAPK Activation and Focal Adhesion Disassembly. J Biol Chem.* 278 (33), 30516-24 (2003). Antagonism of the α2β1 integrin also curbs haptotactic endothelial cell migration, Senger D R et al., a critical step in extravasation of tumor cells into secondary tissues.

It has also recently been shown that human cytomegalovirus (HCMV), which is extremely promiscuous and responsible for significant mortality, requires the presence of α2β1 to penetrate a cell. Feire A L, Koss H, Compton T. *Cellular Integrins Function as Entry Receptors For Human Cytomegalovirus Via a Highly Conserved Disintegrin-Like Domain. Proc Natl Acad Sci USA.* 101 (43), 15470-5 (2004). Likewise, integrin α2β1 has been strongly implicated in rotavirus cell attachment and entry. Graham K L, Halasz P, Tan Y, Hewish M J, Takada Y, Mackow E R, Robinson M K, Coulson B S. *Integrin-using rotaviruses bind alpha2beta1 integrin alpha2 I domain via VP4 DGE sequence and recognize alphaXbeta2 and alphaVbeta3 by using VP7 during cell entry. J Virol.* 77 (18), 9969-78. (2003). Rotaviruses are leading causes of acute gastroenteritis in human infants and young children and animals around the globe. Id. It has been demonstrated that inhibition of the α2β1 integrin forestalls cell binding and infection by rotaviruses. Londrigan S L, Graham K L, Takada Y, Halasz P, Coulson B S. *Monkey rotavirus binding to alpha2beta1 integrin requires the alpha2 I domain and is facilitated by the homologous beta1 subunit. J Virol.* 77 (17), 9486-501 (2003). Similarly, viruses of the Piconaviridae family, such as Echovirus 1 (Echo 1), have also been shown to utilize the α2β1 integrin during the cell-infection cycle. Triantafilou K & Triantafilou M. *A biochemical approach reveals cell-surface molecules utilised by Picornaviridae: Human Parechovirus 1 and Echovirus 1. J Cell Biochem.* 80 (3), 373-81 (2001). Echo viruses are implicated in numerous human pathologies; for example, certain forms of aseptic meningitis and acute respiratory illness are known to be caused by the Echo-1 virus. See, e.g., Kumar R. *Aseptic meningitis: Diagnosis and management. Indian J Pediatr.* 72 (1), 57-63 (2005).

Inhibition of the α2β1 integrin may prove effective in impeding binding and entry of these problematic and medically-significant viruses, and in treatment of cancers and other disease states concerning which α2β1 expression and functionality is a significant factor, and previous efforts have been made to provide compounds possessing α2β1 integrin inhibitory activity. See Takayanagi, M et al., WO 03/008380.

As yet, however, there is an unfulfilled need in these respects. The present invention provides inhibitors of integrin α2β1 and methods for their synthesis and use.

SUMMARY OF THE INVENTION

The present invention is directed to "small" molecule inhibitors of the α2β1 integrin, as well as to methods of their use for treatment of the range of α2β1-affected disease states. These include, inter alia, vascular conditions, diabetes- or rheumatoid arthritis-related conditions, cancers, and viral infections. The present invention represents a versatile and effective, yet selective and safe therapeutic regime for the treatment of α2β1-affected disease states, conditions, and infections. While not intending to be bound by any theory or theories of operation, it is believed that the compounds of the present invention may effect inhibition of the α2β1 integrin by targeting the integrin's "I-like" domain.

In accordance with one embodiment of the invention, there are provided novel compounds of the formula I:

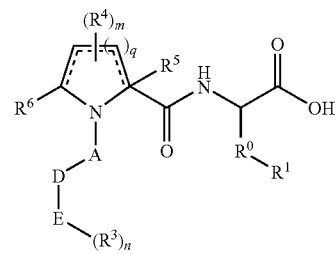

wherein:

$R^0$ is alkylidene;

$R^1$ is NH(aralkyl), NHSO$_2$aryl, NHSO$_2$alkyl, CH$_2$C(=O)alkoxy, NHC(=O)alkyl, NHC(=O)alkoxy, NHC(=O)aralkoxy, NHSO$_2$R$^2$, or NHC(=O)R$^2$;

$R^2$ is aryl, alkyl, aralkyl, aralkoxy, aralkylamino, arylamino, or alkylamino;

Each $R^3$ is independently halo, nitro, aryl, amino, alkyl, alkoxy, NH-Boc, alkylsulfonyl, NHC(=O)alkyl, NHC(=O)aralkyl, or NHC(=O)arylamino;

Each $R^4$ is independently amino, hydroxy, aralkoxy, NH(aryl), or NHC(=O)aryl;

$R^5$ is H or alkyl;

$R^6$ is H or =O;

A is SO$_2$, PO$_2$, CO$_2$, or C=O;

D is optional and may be one or more CH$_2$ groups;

E is aryl or heteroaryl;

n is 0, 1, or 2;

m is 0 or 1;

q is 0, 1, 2, or 3; and, one of the three dashed-line portions may represent a double bond, or a stereoisomer, partial stereoisomer, prodrug, pharmaceutically acceptable salt, hydrate, solvate, acid hydrate, or N-oxide thereof.

In accordance with another embodiment of the invention, there are provided novel compounds of the formula II:

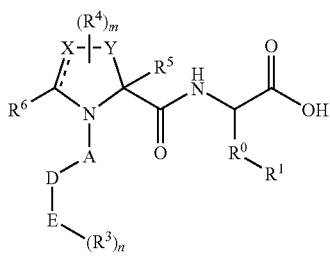

wherein:

$R^0$ is alkylidene;

$R^1$ is NH(aralkyl), NHSO$_2$aryl, NHSO$_2$alkyl, CH$_2$C(=O)alkoxy, NHC(=O)alkyl, NHC(=O)alkoxy, NHC(=O)aralkoxy, NHSO$_2$R$^2$, or NHC(=O)R$^2$;

$R^2$ is aryl, alkyl, aralkyl, aralkoxy, aralkylamino, arylamino, or alkylamino;

Each $R^3$ is independently halo, nitro, aryl, amino, alkyl, alkoxy, NH-Boc, alkylsulfonyl, NHC(=O)alkyl, NHC(=O)aralkyl, or NHC(=O)arylamino;

Each $R^4$ is independently amino, hydroxy, aralkoxy, NH(aryl), or NHC(=O)aryl;

$R^5$ is H or alkyl;

$R^6$ is H or =O;

A is SO$_2$, PO$_2$, CO$_2$, or C=O;

D is optional and may be one or more CH$_2$ groups;

E is aryl or heteroaryl;

X is N, O, or S;

Y is CH$_2$, CR$^7$R$^8$, CCH(CH$_3$), or C(CH$_3$)$_2$;

$R^7$ and $R^8$ are independently H, alkyl, aryl, heteroaryl, alkaryl, or alkyl-heteroaryl;

n is 0, 1, or 2; and, m is 0 or 1, wherein the dashed line may represent a double bond when X is N, or a stereoisomer, partial stereoisomer, prodrug, pharmaceutically acceptable salt, hydrate, solvate, acid hydrate, or N-oxide thereof.

Likewise, in other embodiments, the invention is directed to pharmaceutical compositions comprising a pharmaceutically-acceptable carrier, diluent, or excipient and a compound of formula I or formula II. Other embodiments of the invention provide compositions comprising a stereochemically enriched mixture of compounds of formula I or formula II.

In certain preferred embodiments of formula I, A is SO$_2$. $R^5$ and $R^6$ are each preferably H, q is preferably 1, and $R^0$ is preferably —CH$_2$—. In certain preferred embodiments of formula II, $R^5$ and $R^6$ are each preferably H, Y is preferably CH$_2$, CR$^7$R$^8$, or C(CH$_3$)$_2$, and $R^0$ is preferably —CH$_2$—. In other preferred embodiments of formula II, X is O and Y is CH$_2$. In yet other preferred embodiments of formula II, X is S and Y is CH$_2$, CR$^7$R$^8$, or C(CH$_3$)$_2$. In other embodiments of formula I or II, A is C=O or CO$_2$ and E is phenyl. In yet other preferred embodiments of formula I or II, A is SO$_2$, E is phenyl, and D is optional and represents a bond between A and E. In still other preferred embodiments of formula I or II, A is SO$_2$, E is phenyl, D represents a bond between A and E, and n is 0. With respect to formula I or II, in yet other preferred embodiments, A is SO$_2$, E is phenyl, D represents a bond between A and E, n is 0, and m is 0. In other preferred embodiments of formula I or II, A is SO$_2$, E is phenyl, D represents a bond between A and E, n=1, and $R^3$ is nitro. In still other preferred embodiments of formula I or II, A is SO$_2$, E is phenyl, D represents a bond between A and E, n=2, and $R^3$ is halo. For formula I or formula II compounds, in certain other preferred embodiments, A is SO$_2$, E is phenyl, D represents a bond between A and E, n is 0, and m is 1. In still other preferred embodiments of formula I or II, A is SO$_2$, E is phenyl, D represents a bond between A and E, n is 0, m is 1, and $R^1$ is NHC(=O)R$^2$.

In certain preferred embodiments of compounds of formula I or II, A is SO$_2$, D represents a bond between A and E, E is phenyl, $R^3$ is nitro, n equals 1, and $R^1$ is NH(aralkyl), NHSO$_2$-aryl, CH$_2$C(=O)alkoxy, NHC(=O)alkoxy, NHC(=O)aralkoxy or NHC(=O)R$^2$. In certain other preferred embodiments of compounds of formula I or II, A is SO$_2$, D represents a bond between A and E, E is phenyl, n equals 0, $R^1$ is NHC(=O)R$^2$, and $R^2$ is aryl, aralkylamino, arylamino, aralkyl, aralkoxy, or alkylamino. In still other preferred embodiments, A is SO$_2$, D represents a bond between A and E, E is phenyl, $R^3$ is nitro, n equals 1, $R^1$ is NH(aralkyl), NHSO$_2$aryl, CH$_2$C(=O)alkoxy, NHC(=O)alkoxy, NHC(=O) O-aralkyl or NHC(=O)R$^2$, and $R^2$ is aralkyl, aralkylamino, arylamino, or alkylamino. In certain other preferred embodiments, A is SO$_2$, D represents a bond between A and E, E is phenyl, n equals 2, $R^3$ is alkyl or halo, $R^1$ is NH(aralkyl), NHSO$_2$aryl, CH$_2$C(=O)alkoxy, NHC(=O)alkoxy, NHC(=O)aralkoxy or NHC(=O)R$^2$, and $R^2$ is aralkyl, aralkylamino, arylamino, or alkylamino.

In certain preferred embodiments of formulas I or II, $R^1$ is NH-Boc, NH-Cbz, NH-Bz,

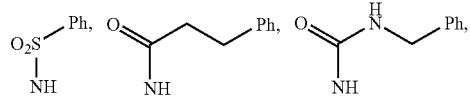

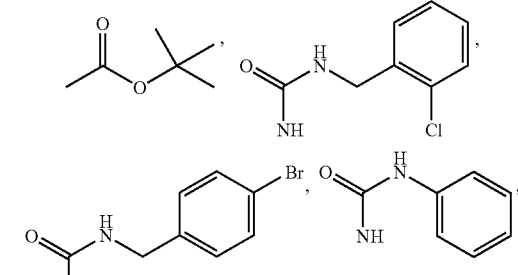

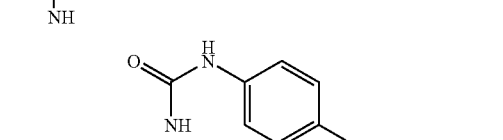

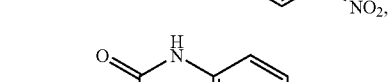

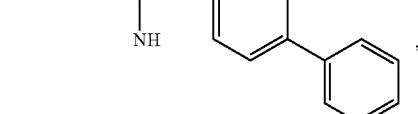

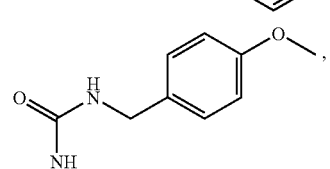

With respect to compounds of formula I or II, in some preferred embodiments, $R^3$ is $NO_2$, $NH_2$, $CH_3$, acetamino, phenyl, NHC(=O)benzyl, NHC(=O)phenylamino, fluoro, chloro, methylsulfonyl, trifluoromethane, or benzyl. In other preferred embodiments of formula I or II, A is $SO_2$, D represents a bond between A and E, E is phenyl, $R^3$ is $NH_2$, $CH_3$, acetamino, phenyl, NHC(=O)phenylamino, methylsulfonyl, or benzyl, n equals 1, and $R^1$ is NH(aralkyl), $NHSO_2$-aryl, $CH_2C$(=O)alkoxy, NHC(=O)alkoxy, NHC(=O) aralkoxy, or NHC(=O)$R^2$. In still other preferred embodiments of formula I or II, A is $SO_2$, D represents a bond between A and E, E is phenyl, $R^3$ is $NH_2$, $CH_3$, acetamino, phenyl, NHC(=O)phenylamino, methylsulfonyl, or benzyl, n equals 1, $R^1$ is NH(aralkyl), $NHSO_2$aryl, $CH_2C$(=O) alkoxy, NHC(=O)alkoxy, NHC(=O)aralkoxy or NHC (=O)$R^2$, and $R^2$ is aralkyl, aralkylamino, arylamino, or alkylamino.

In certain preferred embodiments of formulas I and II, each n is the integer 0, 1, or 2, more preferably, 0 or 1.

In some preferred embodiments of formula I or II, A is $SO_2$, D represents a bond between A and E, E is phenyl, $R^1$ is NH(aralkyl), $NHSO_2$aryl, $CH_2C$(=O)alkoxy, NHC(=O) alkoxy, NHC(=O)aralkoxy or NHC(=O)$R^2$, $R^2$ is aralkyl, aralkylamino, arylamino, alkylamino, and m equals 1. In other preferred embodiments, A is $SO_2$, D represents a bond between A and E, E is phenyl, $R^1$ is NH(aralkyl), $NHSO_2$aryl, $CH_2C$(=O)alkoxy, NHC(=O)alkoxy, NHC(=O)aralkoxy or NHC(=O)$R^2$, $R^2$ is aralkyl, aralkylamino, arylamino, alkylamino, m equals 1, and $R^4$ is hydroxy or phenylmethoxy.

As discussed above, it is known that α2β1 receptor activity on platelets is essential for platelet adhesion to collagen under low and high shear flow conditions. Siljander P R et al., *Blood.* 103 (4):1333-41 (2004). This integrin-mediated adhesion, which occurs early in the hemostatic cascade, is critical to subsequent downstream events that lead to the development of a stable thrombus. Furthermore, outside-in signaling through the α2β1 integrin plays an important role in thrombus formation. Inoue O, Suzuki-Inoue K, Dean W L, Frampton J, Watson S P. *Integrin alpha2beta1 mediates outside-in regulation of platelet spreading on collagen through activation of Src kinases and PLCgamma2. J Cell Biol.* 160 (5): 769-80 (2003). Thus, it is expected that α2β1 integrin contributes significantly to the formation of arterial plaque and thrombosis and is therefore critical to the development of cardiovascular disease; hence the erstwhile preference for weak antithrombotic medicaments like aspirin and clopidogrel, and reluctant use of stronger compounds that alleviate thrombogenesis but that also provoke disruption of hemostasis. Therefore, in certain other embodiments the invention is directed to a method for treating at least one α2β1-affected vascular disorder or condition, comprising the step of administering to a subject in need thereof a composition comprising a therapeutically effective amount of a compound of formula I or formula II.

Likewise, still other embodiments are directed to a method for treating at least one α2β1-affected vascular disorder or condition, comprising the step of administering to a subject in need thereof a composition comprising a therapeutically effective amount of a compound of formula I or II.

In another aspect, the invention is directed to a method for treating as subject suffering from or susceptible to one or more of acute coronary syndromes, stroke, ischaemic complications of peripheral vascular disease, deep vein thrombosis (DVT), myocardial infarction, coronary artery disease, cerebrovascular disease, peripheral arterial disease, diabetes mellitus, atrial fibrillation, congestive heart failure, pulmonary embolism, and other vascular-related disorders, comprising the step of administering to a subject in need thereof a composition comprising a therapeutically effective amount of a compound of formula I or II.

It is believed that α2β1 activity may be closely associated with certain cancers and the processes linked thereto, several types of viral infections, diabetes, rheumatoid arthritis, and numerous other pathologies. Accordingly, the present invention also includes a method for treating a cancer-related, diabetes-related, or rheumatoid disease state, comprising the step of administering to a subject in need thereof a composition comprising a therapeutically effective amount of a compound of formula I or II.

In another aspect, the invention is directed to methods of treatment a subject wherein the subject is suffering from or susceptible to one or more of human melanoma, hepatocellular carcinoma, breast cancer, lung cancer, ovarian cancer, and other cancers and cancer-related disorders.

In certain other embodiments, the invention is directed to methods of treating one or more of rheumatoid arthritis, diabetic retinopathy, and other diabetes- or rheumatoid-related disorders.

In still other embodiments, the invention provides methods for effecting treatment of morphogenesis- or matrix reorganization-affected disease states.

In yet other embodiments, the invention is directed to methods for treating angiogenesis-affected disease states.

In other aspects, the invention provides methods for treating pathologies that are cell migration-, cell proliferation-, cell colonization- or metastasis-affected.

In still other aspects the invention provides methods for treating pathologies that are leukocyte infiltration-affected.

The present invention, in other embodiments, provides methods for treating edema-affected disease states.

Another aspect of the present invention is directed to methods of treating a subject that is suffering from or susceptible to viral infection.

A further aspect of the present invention provides methods for treating viral infections that are at least partially attributable to human cytomegalovirus (HCMV), rotaviruses, Piconaviridae viruses, or related viruses.

DETAILED DESCRIPTION OF ILLUSTRATIVE EMBODIMENTS

As employed above and throughout the disclosure, the following terms and abbreviations, unless otherwise indicated, shall be understood to have the following meanings.

"DAP" denotes 2,3-diaminopropionic acid.

"EDC" stands for 1-(3-Dimethylaminopropyl)-3-ethylcarbodiimide hydrochloride.

"HOBT" means 1-Hydroxybenzotriazole hydrate.

Protective groups are abbreviated according to the system disclosed in Greene, T. W. and Wuts, P. G. M., *Protective Groups in Organic Synthesis* 2d. Ed., Wiley & Sons, 1991, which is incorporated in its entirety herein. For example, "CBZ" or "Cbz" or "Z" stands for carbobenzyloxy or benzyloxycarbonyl, "Boc" or "BOC" represents t-butoxycarbonyl, "Alloc" denotes allyloxycarbonyl, Bz means benzoyl, and "Fmoc" stands for 9-fluorenylmethoxycarbonyl.

In the present disclosure the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "µg" means microgram(s), "eq" means equivalent(s), "h" means hour(s), "µL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein).

"Amino" refers to —$NH_2$ and may include one or more substituents that replace hydrogen.

As used herein, "aryl", "arene", and "aromatic" each refer to an optionally substituted, mono-, di-, tri-, or other multi-cyclic aromatic ring system having from about 5 to about 50 carbon atom ring members (and all combinations and subcombinations of ranges and specific numbers of carbon atoms therein), with from about 6 to about 10 carbon ring atom members being preferred.

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

"Alkylidene" signifies

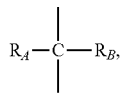

in which $R_A$ and $R_B$ are independently H or alkyl, and wherein alkyl is as previously defined.

As used herein, "aralkyl" refers to alkyl radicals bearing one or more aryl substituents and having from about 6 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkoxy" as used herein refers to the group R—O— where R is an alkyl group, and alkyl is as previously described. "Aralkoxy" stands for R—O—, wherein R is an aralkyl group as previously defined. "Alkylsulfolnyl" means alkyl-$SO_2$—, wherein alkyl is as previously defined.

As used herein, "alkylene" refers to an optionally branched or substituted bivalent alkyl radical having the general formula —$(CH_2)_n$—, where n is 1 to 10. Non-limiting examples include methylene, trimethylene, pentamethylene, and hexamethylene.

As used herein, "heteroaryl" refers to an aryl radical wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members are preferred. Likewise, a "heterocyclic ring" may be an aryl radical wherein one or more of the carbon atom ring members is independently replaced by a heteroatom group selected from the group consisting of S, O, N, and NH. Heterocyclic rings having a total from about 5 to 14 carbon atom ring members and heteroatom ring members are preferred.

"Halo" and "halogen" each refers to a fluoro, chloro, bromo, or iodo moiety, with fluoro, chloro, or bromo being preferred.

The phrase reading "D is optional" means that the substituents to which D is attached may be directly attached to each other. For example, in some preferred embodiments, A is attached directly to E by a bond.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR″), —N,N-disubstituted amino (—N(R″)R″), oxo (=O), carboxy (—COOH), —O—C(=O)R″, —C(=O)R″, —OR″, —C(=O)OR″, -(alkylene)-C(=O)—OR″, —NHC(=O)R″, aminocarbonyl (—C(=O)NH$_2$), —N-substituted aminocarbonyl (—C(=O)NHR″), —N,N-disubstituted aminocarbonyl (—C(=O)N(R″)R″), thiol, thiolato (—SR″), sulfonic acid (—SO$_3$H), phosphonic acid (—PO$_3$H), —P(=O)(OR″)OR″, —S(=O)R″, —S(=O)$_2$R″, —S(=O)$_2$ NH$_2$, —S(=O)$_2$NHR″, —S(=O)$_2$NR″R″, —NHS(=O)$_2$ R″, —NR″S(=O)$_2$R″, —CF$_3$, —CF$_2$CF$_3$, —NHC(=O)NHR″, —NHC(=O)NR″R″, —NR″C(=O)NHR″, —NR″C(=O)NR″R″, —NR″C(=O)R″ and the like. In relation to the aforementioned substituents, each moiety R″ can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula R.H$_2$O, where R is a compound of the invention. A given compound may form more than one hydrate including, for example, monohydrates (R.H$_2$O) or polyhydrates (R.nH$_2$O wherein n is an integer>1) including, for example, dihydrates (R.2H$_2$O), trihydrates (R.3H$_2$O), and the like, or hemihydrates, such as, for example, R.n$_{/2}$H$_2$O, R.n$_{/3}$H$_2$O, R.n$_{/4}$H$_2$O and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, R.n$_{/2}$(solvent), R.n$_{/3}$(solvent), R.n$_{/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

As used herein, the terms "modulation" or "mediation" refer to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

In the present disclosure, the term "inhibitor" is intended to comprise any compound or agent, e.g., antibody, small molecule, peptide, oligopeptide, polypeptide, or protein, preferably small molecule or peptide, that exhibits a partial, complete, competitive and/or inhibitory effect by inhibiting, suppressing, repressing, or decreasing a specific activity, such as platelet activation or adhesion activity, stabilization of thromboses, metastasis, angiogenesis, or viral infection. In certain embodiments, the term preferably refers to an inhibitor of human pathological platelet activity, thus diminishing or blocking, preferably diminishing, some or all of the biological effects of pathological platelet activity. In certain other embodiments, the term preferably refers to an inhibitor of angiogenesis, metastasis, morphogenesis, matrix reorganization, cell migration, cell proliferation, cell colonization, or leukocyte infiltration. In still other embodiments, the term preferably refers to an inhibitor of viral infection.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

The term "vascular system" refers to the vessels and tissue that carry or circulate fluids in the body of an animal, including but not limited to the heart, blood vessels, lymphatic, pulmonary, and portal systems.

The phrases "vascular disease", "vascular disorder", "vascular condition", "vascular pathology", and the like, refer to bodily states affecting the channels and tissue that carry body fluids, such as, but not limited to stroke, deep vein thrombosis (DVT), myocardial infarction, coronary artery disease, cerebrovascular disease, peripheral arterial disease, diabetes mellitus, atrial fibrillation, congestive heart failure, acute coronary syndromes, stroke, pulmonary embolism, and ischaemic complications of peripheral vascular disease.

The term "angiogenesis" refers to the growth, formation, migration, infiltration, or proliferation of blood vessels.

"Piconaviridae viruses" are viruses belonging to the virus family Piconaviridae.

"Subject" or "patient" refers to an embryonic, immature, or adult animal, including the human species, that is treatable with the compositions, and/or methods of the present invention.

Accordingly, the present invention is directed to small-molecule inhibitors of the $\alpha 2\beta 1$ integrin and methods of their use for the treatment of certain vascular disorders and conditions, cancers, diabetes- and arthritis-related conditions, and viral infections. Because the activity of the disclosed compounds of formulas I and II is attributable to $\alpha 2\beta 1$ antagonism and otherwise provides inhibition of particular collagen-induced platelet activity, with respect to treatment of vascular conditions, administration thereof represents an extremely promising and heretofore unachieved strategy for safe antithrombotic therapy and treatment of other disease states associated with the vascular system. For example, it is believed that the present invention described presents a substantial breakthrough in the field of treatment, alleviation, inhibition, and/or prevention of such disorders and conditions, including, but not limited to, stroke, deep vein thrombosis (DVT), myocardial infarction, coronary artery disease, cerebrovascular disease, peripheral arterial disease, atrial fibrillation, and congestive heart failure, acute coronary syndromes, stroke, pulmonary embolism, and ischaemic complications of peripheral vascular disease. In an additional aspect, the present invention represents a promising and distinctive therapy for cancer and cancer-related conditions, including, but not limited to human melanoma, hepatocellular carcinoma, breast, lung, and ovarian cancers, pathological angiogenesis, metastasis, and leukocyte infiltration. In a still further aspect, the invention provides a means of treatment for diabetes- and arthritis-related ailments, such as rheumatoid arthritis, diabetic retinopathy, diabetes mellitus, and related conditions. Administration of the compounds of formula I or II also provides medicinal therapy as against viral infection, for example, by the human cytomegalovirus, rotaviruses, or Piconaviridae viruses, or susceptibility thereto.

In accordance with one embodiment of invention, there are provided novel compounds of the formula I:

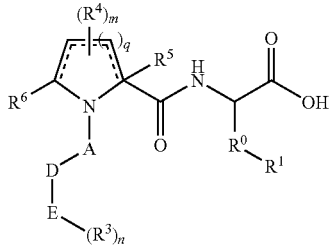

wherein:
R⁰ is alkylidene;
R¹ is NH(aralkyl), NHSO₂aryl, NHSO₂alkyl, CH₂C(=O)alkoxy, NHC(=O)alkyl, NHC(=O)alkoxy, NHC(=O)aralkoxy, NHSO₂R², or NHC(=O)R²;
R² is aryl, alkyl, aralkyl, aralkoxy, aralkylamino, arylamino, or alkylamino;
Each R³ is independently halo, nitro, aryl, amino, alkyl, alkoxy, NH-Boc, alkylsulfonyl, NHC(=O)alkyl, NHC(=O)aralkyl, or NHC(=O)arylamino;
Each R⁴ is independently amino, hydroxy, aralkoxy, NH(aryl), or NHC(=O)aryl;
R⁵ is H or alkyl;
R⁶ is H or =O;
A is SO₂, PO₂, CO₂, or C=O;
D is optional and may be one or more CH₂ groups;
E is aryl or heteroaryl;
n is 0, 1, or 2;
m is 0 or 1;
one of the three dashed-line portions may represent a double bond, and,
q is 0, 1, 2, or 3;
or a stereoisomer, partial stereoisomer, prodrug, pharmaceutically acceptable salt, hydrate, solvate, acid hydrate, or N-oxide thereof.

In accordance with another embodiment of the invention, there are provided novel compounds of the formula II:

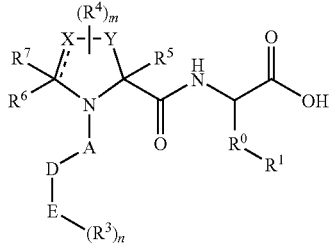

wherein:
R⁰ is alkylidene;
R¹ is NH(aralkyl), NHSO₂aryl, NHSO₂alkyl, CH₂C(=O)alkoxy, NHC(=O)alkyl, NHC(=O)alkoxy, NHC(=O)aralkoxy, NHSO₂R², or NHC(=O)R²;
R² is aryl, alkyl, aralkyl, aralkoxy, aralkylamino, arylamino, or alkylamino;
Each R³ is independently halo, nitro, aryl, amino, alkyl, alkoxy, NH-Boc, alkylsulfonyl, NHC(=O)alkyl, NHC(=O)aralkyl, or NHC(=O)arylamino;
Each R⁴ is independently amino, hydroxy, aralkoxy, NH(aryl), or NHC(=O)aryl;
R⁵ is H or alkyl;
R⁶ is H or =O;
A is SO₂, PO₂, CO₂, or C=O;
D is optional and may be one or more CH₂ groups;
E is aryl or heteroaryl;
X is N, O, or S;
Y is CH₂, CR⁷R⁸, CCH(CH₃), or C(CH₃)₂;
R⁷ and R⁸ are independently H, alkyl, aryl, heteroaryl, alkaryl, or alkyl-heteroaryl;
n is 0, 1, or 2; and,
m is 0 or 1,
wherein the dashed line may represent a double bond when X is N,
or a stereoisomer, partial stereoisomer, prodrug, pharmaceutically acceptable salt, hydrate, solvate, acid hydrate, or N-oxide thereof.

Likewise, in other embodiments, the invention is directed to pharmaceutical compositions comprising a pharmaceutically-acceptable carrier, diluent, or excipient and a compound of formula I or formula II. Other embodiments of the invention provide compositions comprising a stereochemically enriched mixture of compounds of formula I or formula II.

In certain preferred embodiments of formula I, A is SO₂. R⁵ and R⁶ are each preferably H, q is preferably 1, and R⁰ is preferably —CH₂—. In certain preferred embodiments of formula II, R⁵ and R⁶ are each preferably H, Y is preferably CH₂, CR⁷R⁸, or C(CH₃)₂, and R⁰ is preferably —CH₂—. In other preferred embodiments of formula II, X is O and Y is CH₂. In yet other preferred embodiments of formula II, X is S and Y is CH₂, CR⁷R⁸, or C(CH₃)₂. In other embodiments of formula I or II, A is C=O or CO₂ and E is phenyl. In yet other preferred embodiments of formula I or II, A is SO₂, E is phenyl, and D is optional and represents a bond between A and E. In still other preferred embodiments of formula I or II, A is SO₂, E is phenyl, D represents a bond between A and E, and n is 0. With respect to formula I or II, in yet other preferred embodiments, A is SO₂, E is phenyl, D represents a bond between A and E, n is 0, and m is 0. In other preferred embodiments of formula I or II, A is SO₂, E is phenyl, D represents a bond between A and E, n=1, and R³ is nitro. In still other preferred embodiments of formula I or II, A is SO₂, E is phenyl, D represents a bond between A and E, n=2, and R³ is halo. For formula I or formula II compounds, in certain other preferred embodiments, A is SO₂, E is phenyl, D represents a bond between A and E, n is 0, and m is 1. In still other preferred embodiments of formula I or II, A is SO₂, E is phenyl, D represents a bond between A and E, n is 0, m is 1, and R¹ is NHC(=O)R².

In certain preferred embodiments of compounds of formula I or II, A is SO₂, D represents a bond between A and E, E is phenyl, R³ is nitro, n equals 1, and R¹ is NH(aralkyl), NHSO₂-aryl, CH₂C(=O)alkoxy, NHC(=O)alkoxy, NHC(=O)aralkoxy or NHC(=O)R². In certain other preferred embodiments of compounds of formula I or II, A is SO₂, D represents a bond between A and E, E is phenyl, n equals 0, R¹ is NHC(=O)R², and R² is aryl, aralkylamino, arylamino, aralkyl, aralkoxy, or alkylamino. In still other preferred embodiments, A is SO₂, D represents a bond between A and E, E is phenyl, R³ is nitro, n equals 1, R¹ is NH(aralkyl), NHSO₂aryl, CH₂C(=O)alkoxy, NHC(=O)alkoxy, NHC(=O) O-aralkyl or NHC(=O)R², and R² is aralkyl, aralkylamino, arylamino, or alkylamino. In certain other preferred embodiments, A is SO₂, D represents a bond between A and E, E is phenyl, n equals 2, R³ is alkyl or halo, R¹ is NH(aralkyl), NHSO₂aryl, CH₂C(=O)alkoxy, NHC(=O)

alkoxy, NHC(=O)aralkoxy or NHC(=O)R², and R² is aralkyl, aralkylamino, arylamino, or alkylamino.

In certain preferred embodiments of formulas I or II, R¹ is NH-Boc, NH-Cbz, NH-Bz,

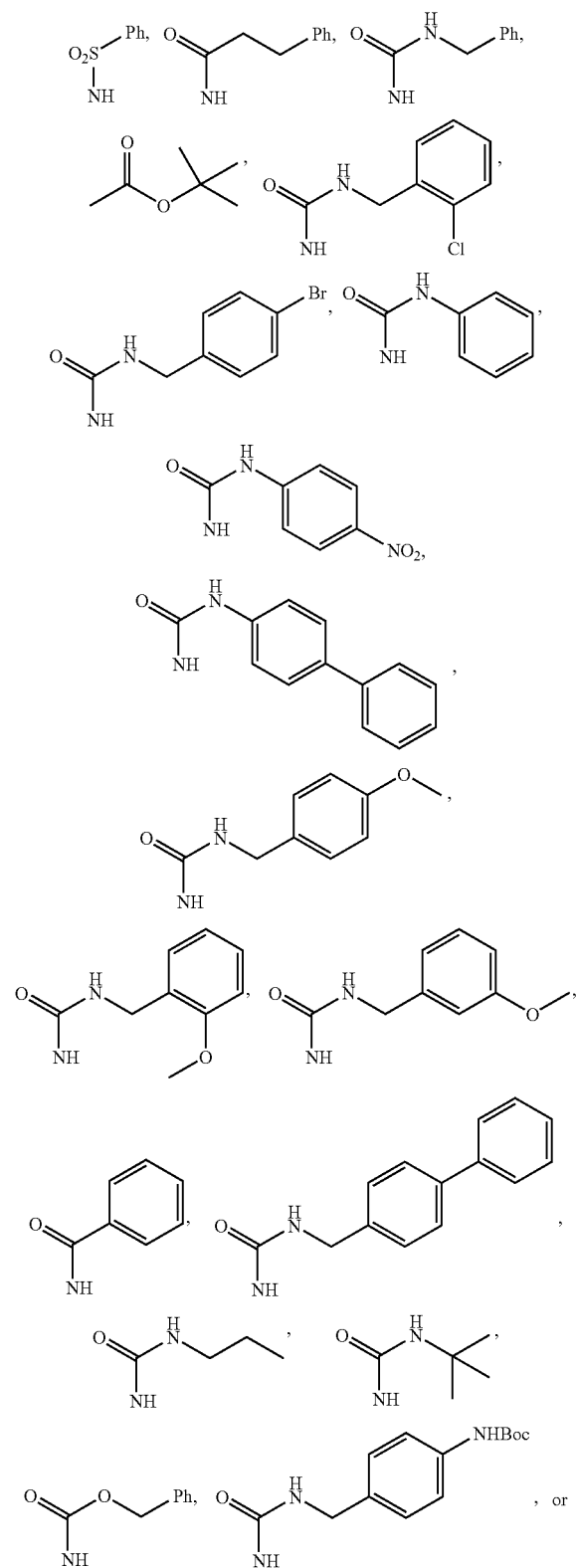

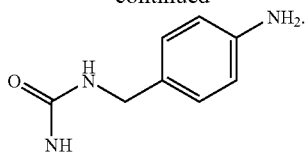

With respect to compounds of formula I or II, in some preferred embodiments, R³ is NO₂, NH₂, CH₃, acetamino, phenyl, NHC(=O)benzyl, NHC(=O)phenylamino, fluoro, chloro, methylsulfonyl, trifluoromethane, or benzyl. In other preferred embodiments of formula I or II, A is SO₂, D represents a bond between A and E, E is phenyl, R³ is NH₂, CH₃, acetamino, phenyl, NHC(=O)phenylamino, methylsulfonyl, or benzyl, n equals 1, and R¹ is NH(aralkyl), NHSO₂-aryl, CH₂C(=O)alkoxy, NHC(=O)alkoxy, NHC(=O)aralkoxy, or NHC(=O)R². In still other preferred embodiments of formula I or II, A is SO₂, D represents a bond between A and E, E is phenyl, R³ is NH₂, CH₃, acetamino, phenyl, NHC(=O)phenylamino, methylsulfonyl, or benzyl, n equals 1, R¹ is NH(aralkyl), NHSO₂aryl, CH₂C(=O)alkoxy, NHC(=O)alkoxy, NHC(=O)aralkoxy or NHC(=O)R², and R² is aralkyl, aralkylamino, arylamino, or alkylamino.

In certain preferred embodiments of formulas I and II, each n is the integer 0, 1, or 2, more preferably, 0 or 1.

In some preferred embodiments of formula I or II, A is SO₂, D represents a bond between A and E, E is phenyl, R¹ is NH(aralkyl), NHSO₂aryl, CH₂C(=O)alkoxy, NHC(=O)alkoxy, NHC(=O)aralkoxy or NHC(=O)R², R² is aralkyl, aralkylamino, arylamino, alkylamino, and m equals 1. In other preferred embodiments, A is SO₂, D represents a bond between A and E, E is phenyl, R¹ is NH(aralkyl), NHSO₂aryl, CH₂C(=O)alkoxy, NHC(=O)alkoxy, NHC(=O)aralkoxy or NHC(=O)R², R² is aralkyl, aralkylamino, arylamino, alkylamino, m equals 1, and R⁴ is hydroxy or phenylmethoxy.

In certain preferred embodiments of compounds of formulas I and II, the compound is selected from the group consisting of:

3-tert-Butoxycarbonylamino-2-{[1-(4-nitro-benzenesulfonyl)-pyrrolidine-2-carbonyl]-amino}-propionic acid;
3-Benzyloxycarbonylamino-2-{[1-(4-nitro-benzenesulfonyl)-pyrrolidine-2-carbonyl]-amino}-propionic acid;
3-Benzoylamino-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-3-(3-phenyl-propionylamino)-propionic acid;
3-(3-Benzyl-ureido)-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-pentanedioic acid 5-tert-butyl ester;
3-[3-(2-Chloro-benzyl)-ureido]-2-{[1-(4-nitro-benzenesulfonyl)-pyrrolidine-2-carbonyl]-amino}-propionic acid;
3-[3-(4-Bromo-benzyl)-ureido]-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-3-(3-phenyl-ureido)-propionic acid;
2-{[1-(4-Nitro-benzenesulfonyl)-pyrrolidine-2-carbonyl]-amino}-3-[3-(4-nitro-phenyl)-ureido]-propionic acid;
3-(3-Biphenyl-4-yl-ureido)-2-{[1-(4-nitro-benzenesulfonyl)-pyrrolidine-2-carbonyl]-amino}-propionic acid;
3-[3-(4-Methoxy-benzyl)-ureido]-2-{[1-(4-nitro-benzenesulfonyl)-pyrrolidine-2-carbonyl]-amino}-propionic acid;
3-[3-(2-Methoxy-benzyl)-ureido]-2-{[1-(4-nitro-benzenesulfonyl)-pyrrolidine-2-carbonyl]-amino}-propionic acid;

3-[3-(3-Methoxy-benzyl)-ureido]-2-{[1-(4-nitro-benzene-sulfonyl)-pyrrolidine-2-carbonyl]-amino}-propionic acid;
3-(3-Biphenyl-4-ylmethyl-ureido)-2-{[1-(4-nitro-benzene-sulfonyl)-pyrrolidine-2-carbonyl]-amino}-propionic acid;
2-{[1-(4-Nitro-benzenesulfonyl)-pyrrolidine-2-carbonyl]-amino}-3-(3-propyl-ureido)-propionic acid;
3-(3-tert-Butyl-ureido)-2-{[1-(4-nitro-benzenesulfonyl)-pyrrolidine-2-carbonyl]-amino}-propionic acid;
3-[3-(4-tert-Butoxycarbonylamino-benzyl)-ureido]-2-{[1-(4-nitro-benzenesulfonyl)-pyrrolidine-2-carbonyl]-amino}-propionic acid;
3-[3-(4-Amino-benzyl)-ureido]-2-{[1-(4-nitro-benzene-sulfonyl)-pyrrolidine-2-carbonyl]-amino}-propionic acid;
2-[(1-Benzenesulfonyl-pyrrolidine-2-carbonyl)-amino]-3-(3-benzyl-ureido)-propionic acid;
2-{[1-(4-Acetylamino-benzenesulfonyl)-pyrrolidine-2-carbonyl]-amino}-3-(3-benzyl-ureido)-propionic acid;
3-(3-Benzyl-ureido)-2-[(1-phenylmethanesulfonyl-pyrrolidine-2-carbonyl)-amino]-propionic acid;
2-[2-(3-Benzyl-ureido)-1-carboxy-ethylcarbamoyl]-pyrrolidine-1-carboxylic acid benzyl ester;
3-(3-Benzyl-ureido)-2-{[1-(biphenyl-4-sulfonyl)-pyrrolidine-2-carbonyl]-amino}-propionic acid;
2-{[1-(4-Amino-benzenesulfonyl)-pyrrolidine-2-carbonyl]-amino}-3-(3-benzyl-ureido)-propionic acid;
2-[(1-Benzoyl-pyrrolidine-2-carbonyl)-amino]-3-(3-benzyl-ureido)-propionic acid;
3-(3-Benzyl-ureido)-2-{[1-(toluene-4-sulfonyl)-pyrrolidine-2-carbonyl]-amino}-propionic acid;
3-(3-Benzyl-ureido)-2-{[1-(naphthalene-1-sulfonyl)-pyrrolidine-2-carbonyl]-amino}-propionic acid;
3-(3-Benzyl-ureido)-2-{[1-(naphthalene-2-sulfonyl)-pyrrolidine-2-carbonyl]-amino}-propionic acid;
3-[3-(4-Amino-benzyl)-ureido]-2-[(1-benzenesulfonyl-pyrrolidine-2-carbonyl)-amino]-propionic acid;
3-(3-Benzyl-ureido)-2-{[1-(3,5-dimethyl-benzenesulfonyl)-pyrrolidine-2-carbonyl]-amino}-propionic acid;
3-(3-Benzyl-ureido)-2-{[1-(4-phenylacetylamino-benzene-sulfonyl)-pyrrolidine-2-carbonyl]-amino}-propionic acid;
3-(3-Benzyl-ureido)-2-({1-[4-(3-phenyl-ureido)-benzene-sulfonyl]-pyrrolidine-2-carbonyl}-amino)-propionic acid;
3-(3-Benzyl-ureido)-2-{[1-(naphthalene-2-sulfonyl)-pyrrolidine-2-carbonyl]-amino}-propionic acid;
2-[(1-Benzenesulfonyl-pyrrolidine-2-carbonyl)-amino]-3-[3-(2-chloro-benzyl)-ureido]-propionic acid;
2-[(1-Benzenesulfonyl-pyrrolidine-2-carbonyl)-amino]-3-(3-phenyl-ureido)-propionic acid;
2-[(1-Benzenesulfonyl-pyrrolidine-2-carbonyl)-amino]-3-(3-phenyl-propionylamino)-propionic acid;
2-[(1-Benzenesulfonyl-pyrrolidine-2-carbonyl)-amino]-3-benzoylamino-propionic acid;
2-[(1-Benzenesulfonyl-pyrrolidine-2-carbonyl)-amino]-3-benzyloxycarbonylamino-propionic acid;
2-[(1-Benzenesulfonyl-pyrrolidine-2-carbonyl)-amino]-3-[3-(2-methoxy-benzyl)-ureido]-propionic acid;
2-[(1-Benzenesulfonyl-pyrrolidine-2-carbonyl)-amino]-3-[3-(3-methoxy-benzyl)-ureido]-propionic acid;
2-[(1-Benzenesulfonyl-pyrrolidine-2-carbonyl)-amino]-3-(3-propyl-ureido)-propionic acid;
3-(3-Benzyl-ureido)-2-{[1-(3,5-difluoro-benzenesulfonyl)-pyrrolidine-2-carbonyl]-amino}-propionic acid;
3-(3-Benzyl-ureido)-2-{[1-(4-methanesulfonyl-benzene-sulfonyl)-pyrrolidine-2-carbonyl]-amino}-propionic acid;
2-[(1-Benzenesulfonyl-pyrrolidine-2-carbonyl)-amino]-3-(3-tert-butyl-ureido)-propionic acid;
2-[(1-Benzenesulfonyl-4-benzyloxy-pyrrolidine-2-carbonyl)-amino]-3-(3-benzyl-ureido)-propionic acid;
2-[(1-Benzenesulfonyl-4-hydroxy-pyrrolidine-2-carbonyl)-amino]-3-(3-benzyl-ureido)-propionic acid;
3-(3-Benzyl-ureido)-2-{[1-(3,5-dichloro-benzenesulfonyl)-pyrrolidine-2-carbonyl]-amino}-propionic acid;
3-(3-Benzyl-ureido)-2-{[1-(3,5-bis-trifluoromethyl-benze-nesulfonyl)-pyrrolidine-2-carbonyl]-amino}-propionic acid;
2-[(3-Benzenesulfonyl-5,5-dimethyl-thiazolidine-4-carbonyl)-amino]-3-(3-benzyl-ureido)-propionic acid;
2-[(1-Benzenesulfonyl-piperidine-2-carbonyl)-amino]-3-(3-benzyl-ureido)-propionic acid;
2-[(1-Benzenesulfonyl-2,5-dihydro-1H-pyrrole-2-carbonyl)-amino]-3-(3-benzyl-ureido)-propionic acid; and,
2-[(1-Benzenesulfonyl-pyrrolidine-2-carbonyl)-amino]-3-(3-benzyl-ureido)-propionic acid.

The compounds employed in the present invention may exist in prodrug form. As used herein, "prodrug" is intended to include any covalently bonded carriers which release the active parent drug, for example, as according to the formulas or compounds employed in the methods of the present invention in vivo when such prodrug is administered to a subject. Since prodrugs are known to enhance numerous desirable qualities of pharmaceuticals (e.g., solubility, bioavailability, manufacturing, etc.) the compounds of the present invention may, if desired, be delivered in prodrug form. Thus, the present invention contemplates methods of delivering prodrugs. Prodrugs of the compounds employed in the present invention, for example, according to formula I or formula II, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis 2d. Ed., Wiley & Sons*, 1991.

In a further aspect, the invention relates to a pharmaceutical composition comprising a compound of formula I or II and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum metahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including, for example, the compounds of formula I or II may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

EXAMPLES

Examples 1-7 provide schemes for the synthesis of representative compounds, including both solution-state and solid-phase reactions and sample embodiments. Example 8 is a mass spectrometry and NMR assay of the resulting compounds. Example 9 illustrates a platelet adhesion assay for determining $IC_{50}$ values of representative compounds. Example 10 presents a test to assess the in vivo activity of the inventive compounds as compared with an untreated arterial injury. Example 11 provides a test designed to assess the specificity of representative embodiments of the instant compounds for the $\alpha 2\beta 1$ integrin.

Example 1

Solution-State Synthesis of Some Preferred Embodiments

Synthesis of some preferred embodiments was accomplished as illustrated in the following generalized schematic and as described below:

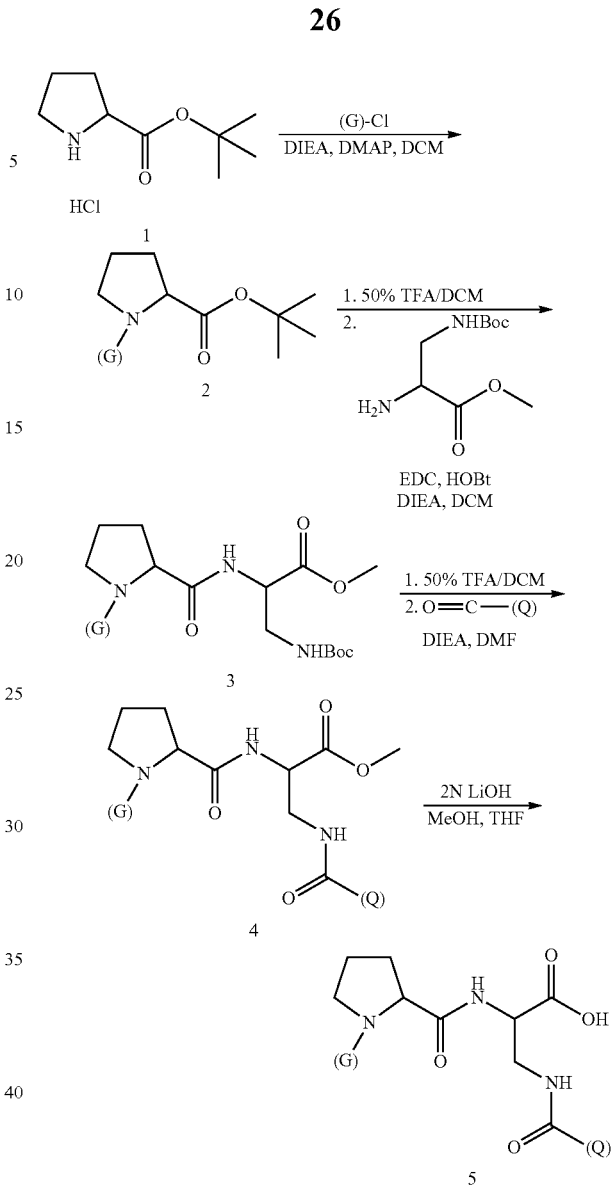

To a solution of (S)-tert-butyl pyrrolidine-2-carboxylate 1, DIEA, and DMAP in dry DCM was added (G)-Cl, where (G)-Cl is an arene sulfonyl chloride, benzyl sulfonyl chloride, benzyloxycarbonyl chloride, or benzoyl chloride. The resulting mixture was stirred at room temperature overnight. The solvent was evaporated and the residue was dissolved with EtOAc. The organic layer was washed with 10% citric acid, saturated $NaHCO_3$ (aq), saturated NaCl (aq) and dried with $Na_2SO_4$. The solution was filtered and concentrated. The product was purified by column chromatography (Hexane/EtOAc 5:1) to give compound 2.

The tert-butyl group of compound 2 was removed by treatment of 50% TFA in DCM. After stirring for 1 h, the TFA and DCM were removed under vacuum. To a solution of crude acid and H-Dap(Boc)-OMe HCl in DCM were added EDC, HOBT, and DIEA. The resulting mixture was stirred at room temperature overnight. The solvent was evaporated and the residue was dissolved with EtOAc. The organic layer was washed with 10% citric acid, saturated $NaHCO_3$ (aq), saturated NaCl (aq) and dried with $Na_2SO_4$. The solution was filtered and concentrated. The product was purified by column chromatography (Hexane/EtOAc 1.5:1) to give compound 3.

The Boc protective group of compound 3 was removed by treatment of 50% TFA in DCM. After stirring for 1 h, the TFA and DCM were removed under vacuum. To a solution of O=C-(Q), where (Q) was alkoxy, aryl, aryloxy, aralkyl, aralkoxy, aralkylamino, NH$_2$(aralkylamino), NO$_2$(arylamino), NHBoc(aralkylamino), arylamino, para-biphenylamino, alkoxy-benzylamino, C-Biphenyl-4-yl-methylamino, or alkylamino, as is apparent to those skilled in the art from the compounds depicted in Table 1, in DCM was added Et$_3$N. The resulting mixture was stirred at room temperature overnight. The solvent was evaporated and the residue was dissolved with EtOAc. The organic layer was washed with citric acid, saturated NaHCO$_3$ (aq), saturated NaCl (aq) and dried with Na$_2$SO$_4$. The solution was filtered and concentrated. The product was purified by column chromatography (Hexane/EtOAc 1:2) to give compound 4.

To a solution of compound 4 in MeOH was added LiOH. The resulting mixture was stirred. The MeOH was removed under reduced pressure. The aqueous solution was diluted with H$_2$O and washed with Et$_2$O followed by acidification with HCl. The white precipitate was extracted in EtOAc. Purification was carried out on HPLC to give compound 5.

Example 2

Solution-State Synthesis 3-(3-Benzyl-ureido)-2-{[1-(4-nitro-benzenesulfonyl)-pyrrolidine-2-carbonyl]-amino}-propionic acid The following schematic and description illustrate a particular example of the solution-state synthesis of a preferred compound:

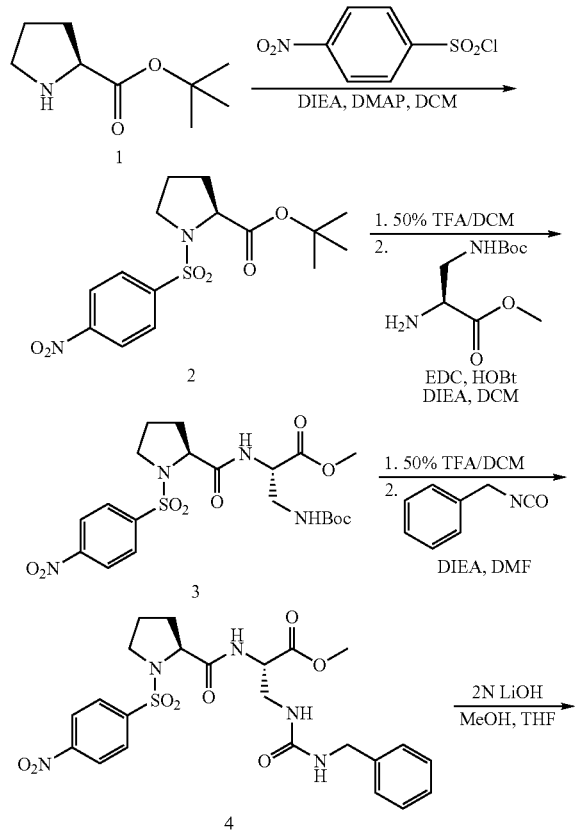

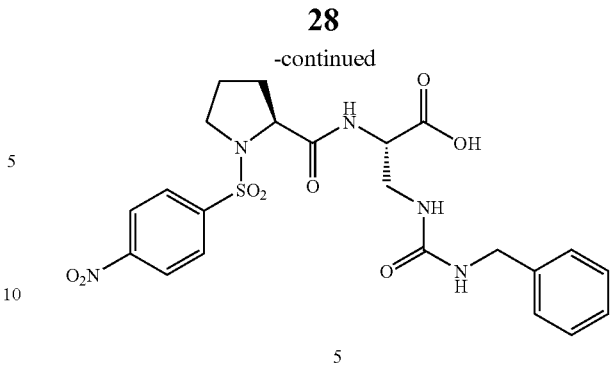

5

To a solution of (S)-tert-butyl pyrrolidine-2-carboxylate (780 mg, 3.755 mmol), DIEA (1.962 ml, 11.265 mmol)), and DMAP (91.7 mg, 0.751 mmol) in dry DCM (20 ml) was added 4-nitrobenzenesulfonyl chloride (1.314 g, 5.633 mmol). The resulting mixture was stirred at room temperature overnight. The solvent was evaporated and the residue was dissolved with EtOAc. The organic layer was washed with 10% citric acid, saturated NaHCO$_3$ (aq), saturated NaCl (aq) and dried with Na$_2$SO$_4$. The solution was filtered and concentrated. The product was purified by column chromatography (Hexane/EtOAc 5:1) to give compound 2 (1.257 g, 94%).

The t-Bu group of compound 2 (1.5 g, 4.21 mmol) was removed by treatment of 50% TFA in DCM. After stirring for 1 h, the TFA and DCM were removed under vacuum. To a solution of crude acid and H-Dap(Boc)-OMe HCl (1.18 g, 4.63 mmol) in DCM (40 ml) were added EDC (0.99 g, 5.05 mmol), HOBT (0.68 g, 5.05 mmol), and DIEA (1.76 ml, 10.1 mmol). The resulting mixture was stirred at room temperature overnight. The solvent was evaporated and the residue was dissolved with EtOAc. The organic layer was washed with 10% citric acid, saturated NaHCO$_3$ (aq), saturated NaCl (aq) and dried with Na$_2$SO$_4$. The solution was filtered and concentrated. The product was purified by column chromatography (Hexane/EtOAc 1.5:1) to give compound 3 (1.96 g, 93%).

The Boc group of compound 3 (68.2 mg, 0.136 mmol) was removed by treatment of 50% TFA in DCM. After stirring for 1 h, the TFA and DCM were removed under vacuum.

To a solution of crude amine and benzyl isocyanate (33.4 μl, 0.273 mmol) in DCM (2 ml) was added Et$_3$N (57 μl, 0.409 mmol). The resulting mixture was stirred at room temperature overnight. The solvent was evaporated and the residue was dissolved with EtOAc. The organic layer was washed with 10% citric acid, saturated NaHCO$_3$ (aq), saturated NaCl (aq) and dried with Na$_2$SO$_4$. The solution was filtered and concentrated. The product was purified by column chromatography (Hexane/EtOAc 1:2) to give compound 4 (69 mg, 95%).

To a solution of compound 4 (43 mg, 0.084 mmol) in MeOH (2 ml) was added 2N LiOH (84 μl, 0.167 mmol). The resulting mixture was stirred for 24 hr. The MeOH was removed under reduced pressure. The aqueous solution was diluted with H$_2$O (20 ml) and washed with Et$_2$O followed by acidification to pH 3-4 with 1N HCl. The white precipitate was extracted in EtOAc. Purification was carried out on HPLC to give compound 5, the complete 3-(3-Benzyl-ureido)-2-{[1-(4-nitro-benzenesulfonyl)-pyrrolidine-2-carbonyl]-amino}-propionic acid molecule, which is shown in Table 1 as Compound 5.

Example 3

Solution-State Synthesis of 2-{[1-(4-Nitro-benzene-sulfonyl)-pyrrolidine-2-carbonyl]-amino}-pentanedioic acid 5-tert-butyl ester In some instances, the $R^1$ moiety is linked to the remainder of the molecule by a nitrogen heteroatom. In other instances, however, the nitrogen is replaced by a carbon. It will be readily apparent to those skilled in the art how to create compounds of this variety, but for purposes of clarification, synthesis of one such embodiment, shown as Compound 6 in Table 1, is illustrated in the following schematic:

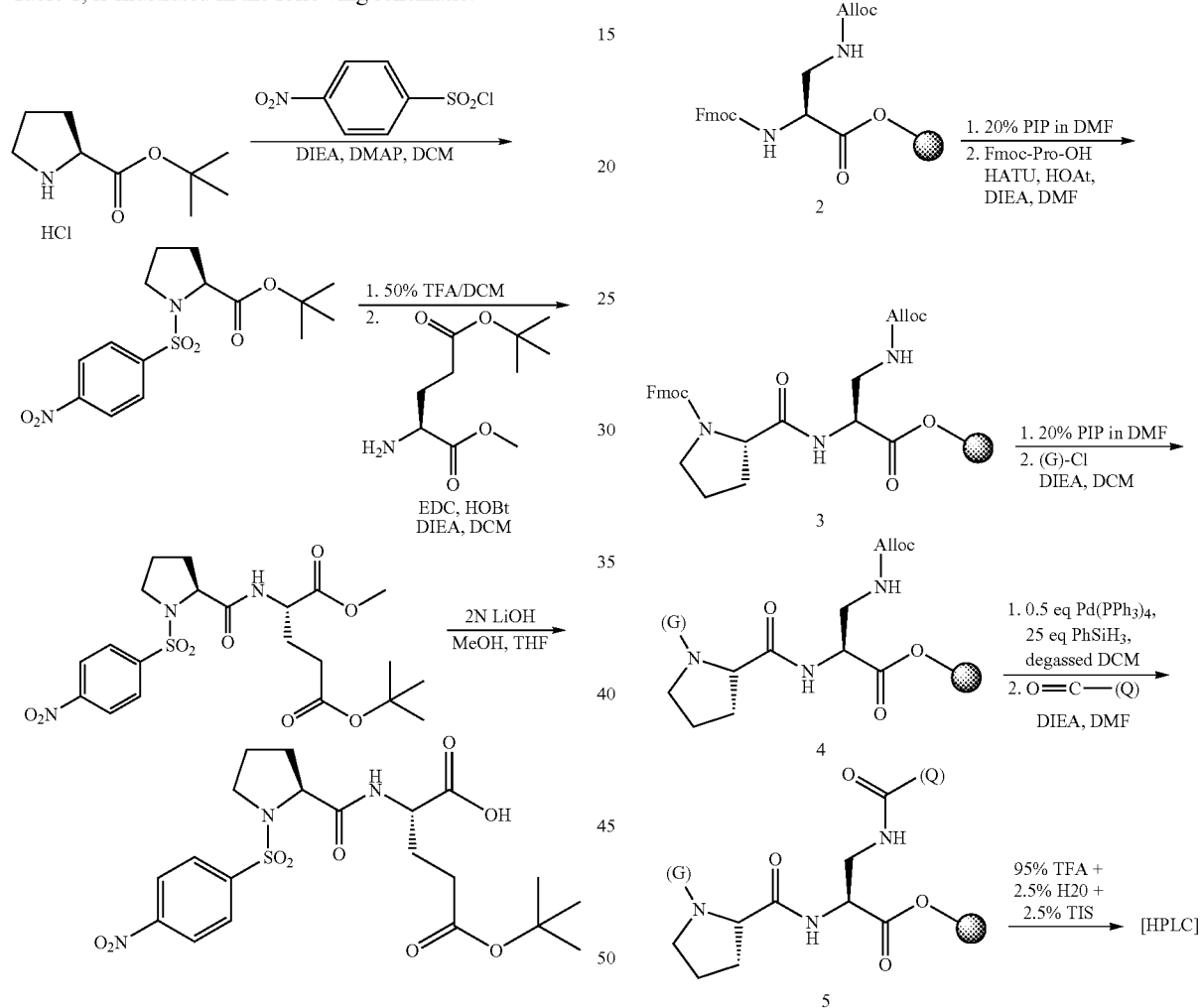

Example 4

Solid-Phase Synthesis

A solid-phase synthesis, which made use of a 4-(Bromomethyl)phenoxymethyl polystyrene resin, was also used to synthesize the compounds of the invention wherever an undesired racemization of the stereocenter 2,3-diaminopropionic acid (DAP) motif was observed while conducting the solution-state method. This methodology completely eliminated the problem of unbidden racemization of the DAP stereocenter. Therefore, some preferred embodiments were created according to the following generalized schematic and as described below:

First, the 4-(Bromomethyl)phenoxymethyl polystyrene resin (represented by Br-⬤) (Novabiochem) was swelled in DMF. Fmoc-Dap(Alloc)-OH (1.5 eq) (Bachem), CsI (1.5 eq), and DIEA (2 eq) were added and the reaction was stirred at room temperature overnight. The resin was filtered and washed repeatedly with DMF and MeOH.

After deprotecting the Fmoc group by treatment of 20% PIP in DMF, the resin was washed with DMF. This resin was then suspended with DMF and reacted with Fmoc-Pro-OH (3 eq), HATU (3 eq), HOAT (3 eq), and DIEA (6 eq) for 3 h. The resin was filtered and washed with DMF. After deprotecting the Fmoc group by treatment of 20% PIP in DMF, the resin was washed with DMF. This resin was then suspended with DCM and reacted with (G)-Cl, where (G)-Cl is an arene sulfonyl chloride, benzyl sulfonyl chloride, benzyloxycarbonyl chloride, or benzoyl chloride, and DIEA (6 eq) overnight. The resin was filtered, washed with DCM and DMF, and dried.

To a peptide resin washed with oxygen-free DCM in the presence of Argon was added a solution of PhSiH$_3$ and the resin was stirred. Subsequently, Pd (PPh$_3$)$_4$ (0.5 eq) was added under Argon, and the reaction was stirred under Argon. Then, the resin was washed repeatedly with DCM and DMF. This resin was then suspended with DMF and reacted with O=C-(Q), where (Q) was alkoxy, aryl, aryloxy, aralkyl, aralkoxy, aralkylamino, NH$_2$(aralkylamino), NO$_2$(arylamino), NHBoc(aralkylamino), arylamino, para-biphenylamino, alkoxy-benzylamino, C-Biphenyl-4-yl-methylamino, or alkylamino, and DIEA (6 eq) overnight. The resin was filtered, washed with DMF and DCM, and dried.

The compound was cleaved from the resin by treatment of 95% TFA, 2.5% TIS, and 2.5% water. Purification was carried out on HPLC.

Example 5

Solid-Phase Synthesis of 3-[3-(3-Methoxy-benzyl)-ureido]-2-{[1-(4-nitro-benzenesulfonyl)-pyrrolidine-2-carbonyl]-amino}-propionic acid The following schematic and description provide a specific example of solid-phase synthesis of a preferred embodiment:

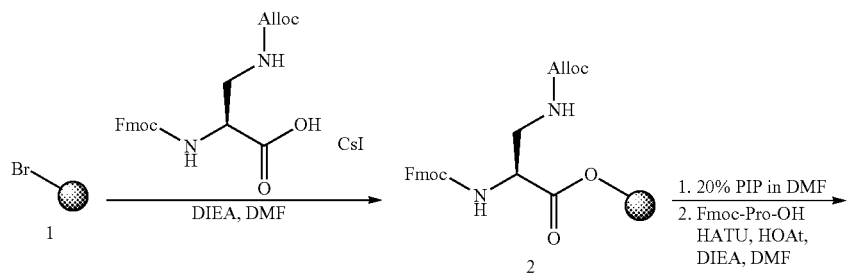

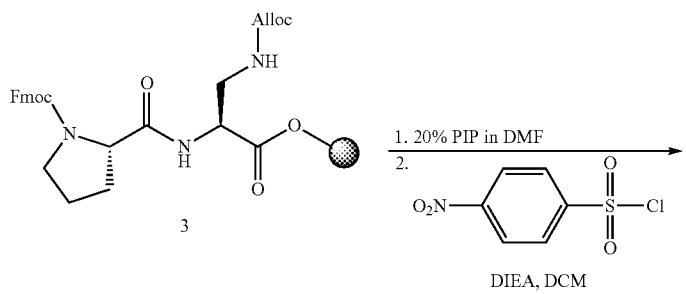

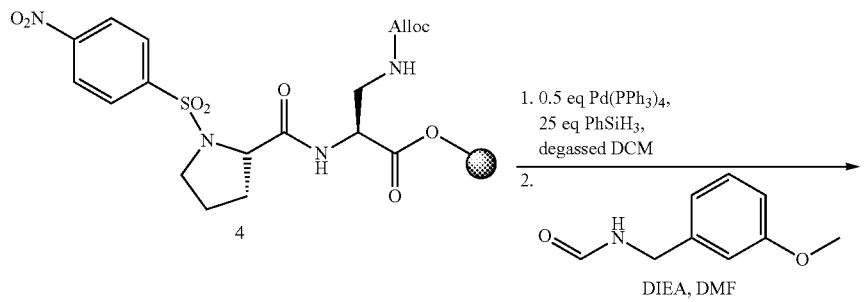

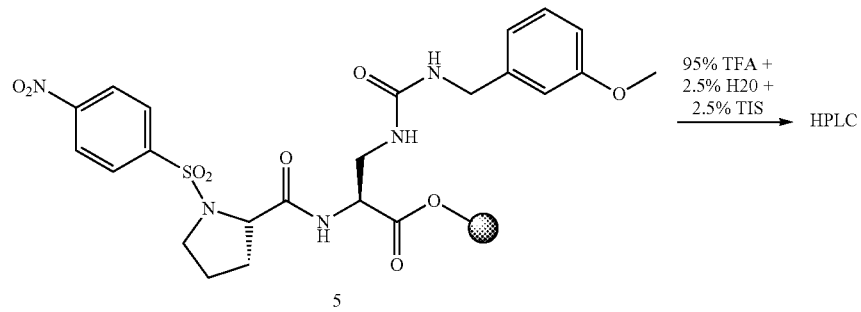

The 4-(Bromomethyl)phenoxymethyl polystyrene resin was swelled in DMF (10 mL/g resin). Fmoc-DAP(Alloc)-OH (1.5 eq), CsI (1.5 eq), and DIEA (2 eq) were added and the reaction was stirred at room temperature overnight. The resin was filtered and washed repeatedly with DMF (1*1 min, 1*10 min, 1*1 min) and MeOH (1*1 min, 1*10 min, 1*1 min).

After deprotecting the Fmoc group by treatment of 20% PIP in DMF, the resin was washed with DMF (1*1 min, 1*10 min, 3*1 min). The resin was then suspended with DMF and reacted with Fmoc-Pro-OH (3 eq), HATU (3 eq), HOAT (3 eq), and DIEA (6 eq) for 3 h. The resin was filtered and washed with DMF (1*1 min, 1*10 min, 3*1 min). After deprotecting the remaining Fmoc group by treatment of 20% PIP in DMF, the resin was washed with DMF (1*1 min, 1*10 min, 3*1 min). This resin was then suspended with DCM and reacted with 4-Nitro-benzenesulfonyl chloride (3 eq), DIEA (6 eq) overnight. The resin was filtered, washed with DCM (1*1 min, 1*10 min, 1*1 min) and DMF (1*1 min, 1*10 min, 1*1 min), and dried.

A solution of $PhSiH_3$ (24 eq) was added to the peptide resin washed with oxygen-free DCM in the presence of Argon, and the resin was stirred for 2 min. Subsequently, Pd $(PPh_3)_4$ (0.5 eq) was added under Argon. The reaction was stirred for 2 hr under Argon. Then, the resin was washed repeatedly with DCM (1*1 min, 1*10 min, 1*1 min) and DMF (1*1 min, 1*10 min, 1*1 min). This resin was then suspended with DMF and reacted with O=C (5-Methoxybenzylamino) (3 eq) and DIEA (6 eq) overnight. The resin was filtered, washed with DMF (1*1 min, 1*10 min, 1*1 min) and DCM (1*1 min, 1*10 min, 1*1 min), and dried.

The 3-[3-(3-Methoxy-benzyl)-ureido]-2-{[1-(4-nitro-benzenesulfonyl)-pyrrolidine-2-carbonyl]-amino}-propionic acid molecule, shown in Table 1 as Compound 14, was cleaved from the resin by treatment of 95% TFA, 2.5% TIS, and 2.5% water. Purification was carried on HPLC.

Example 6

Solid-State Synthesis of 2-[(1-Benzenesulfonyl-4-hydroxy-pyrrolidine-2-carbonyl)-amino]-3-(3-benzyl-ureido)-propionic acid Some of the compounds of the present invention feature a substituted heterocyclic ring. Compounds 46 and 47, shown in Table 1, are two such examples. In light of the preceding disclosure, it will be readily apparent to one skilled in the art how to create such compounds. However, for purposes of clarification, a schematic of the solid-state synthesis of 2-[(1-Benzenesulfonyl-4-hydroxy-pyrrolidine-2-carbonyl)-amino]-3-(3-benzyl-ureido)-propionic acid, i.e., Compound 47, is provided:

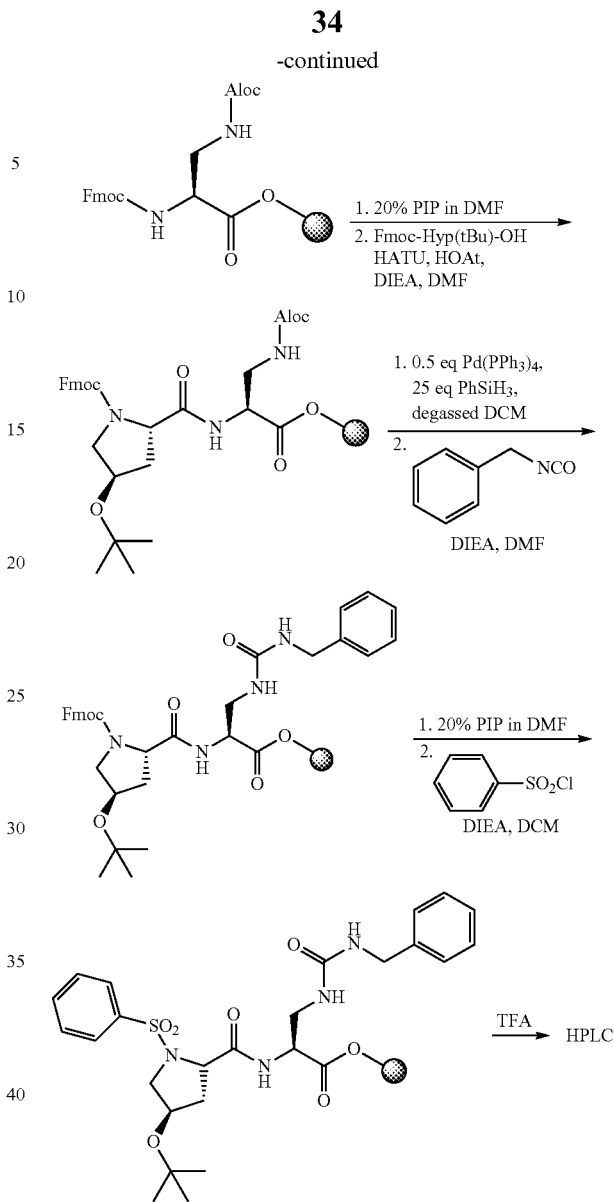

Example 6

Alternative Method for Solid-Phase Synthesis

Other preferred embodiments were created according to the following alternative method of solid-phase synthesis, as depicted and as described below:

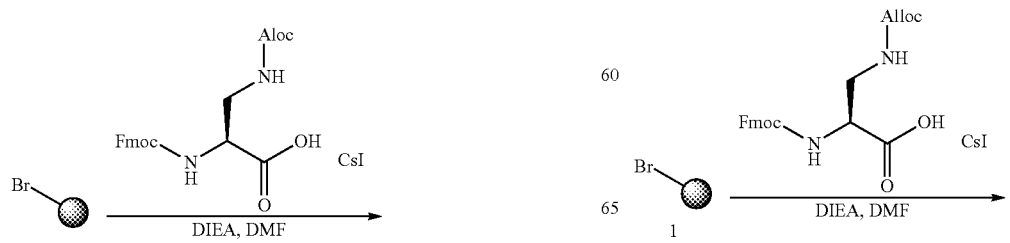

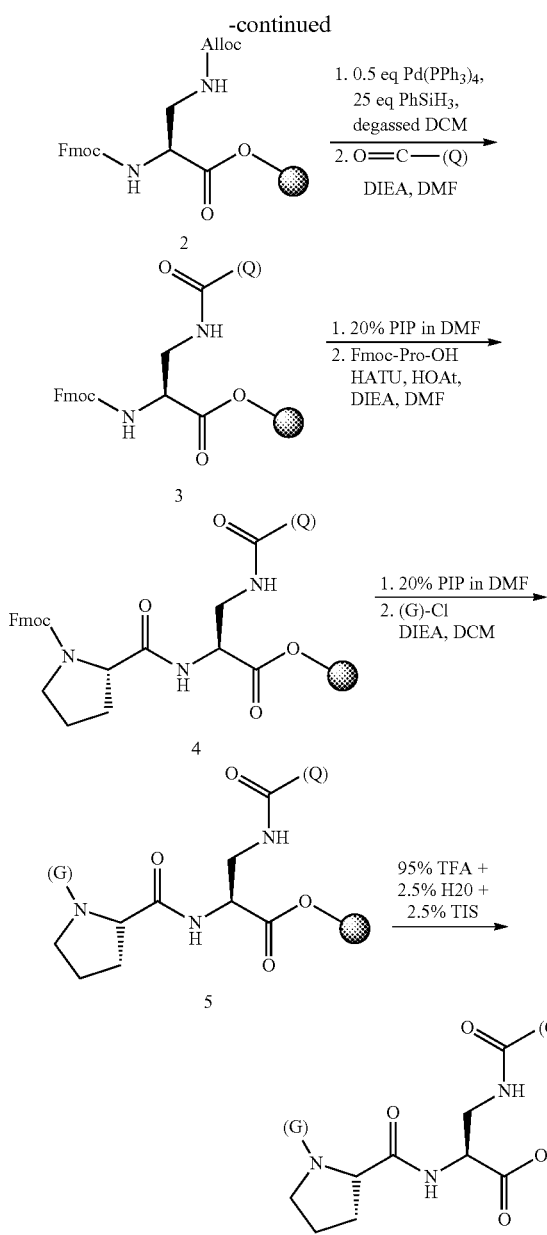

then suspended with DMF and reacted with Fmoc-Pro-OH (3 eq), HATU (3 eq), HOAT (3 eq), and DIEA (6 eq) for 3 h. The resin was filtered and washed with DMF. After deprotecting the Fmoc group by treatment of 20% PIP in DMF, the resin was washed with DMF. This resin was then suspended with DCM and reacted with (G)-Cl, where (G)-Cl is an arene sulfonyl chloride, benzyl sulfonyl chloride, benzyloxycarbonyl chloride, or benzoyl chloride, and DIEA (6 eq) overnight. The resin was filtered, washed with DCM and DMF, and dried.

The compound was cleaved from the resin by treatment of 95% TFA, 2.5% TIS, and 2.5% water. Purification was carried out on HPLC.

Example 7

Solid-Phase Synthesis of 3-(3-Benzyl-ureido)-2-{[1-(4-nitro-benzenesulfonyl)-pyrrolidine-2-carbonyl]-amino}-propionic acid, Using Alternative Method An alternative-method solid-phase synthesis of a preferred embodiment is provided in the following schematic and description:

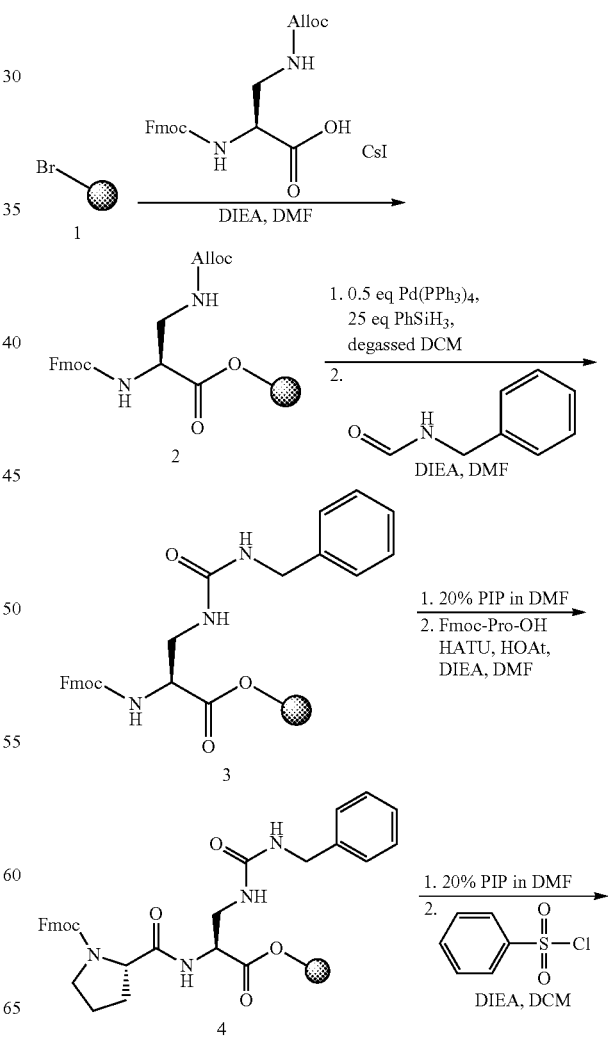

First, the 4-(Bromomethyl)phenoxymethyl polystyrene resin (represented by Br-●) was swelled in DMF. Fmoc-Dap (Alloc)-OH (1.5 eq), CsI (1.5 eq), and DIEA (2 eq) were added and the reaction was stirred at room temperature overnight. The resin was filtered and washed repeatedly with DMF and MeOH.

To a peptide resin washed with oxygen-free DCM in the presence of Argon was added a solution of PhSiH$_3$ and the resin was stirred. Subsequently, Pd (PPh$_3$)$_4$ (0.5 eq) was added under Argon, and the reaction was stirred under Argon. Then, the resin was washed repeatedly with DCM and DMF. This resin was then suspended with DMF and reacted with O═C-(Q), where (Q) was alkoxy, aryl, aryloxy, aralkyl, aralkoxy, aralkylamino, NH$_2$(aralkylamino), NO$_2$(arylamino), NHBoc(aralkylamino), arylamino, para-biphenylamino, alkoxy-benzylamino, C-Biphenyl-4-yl-methylamino, or alkylamino, and DIEA (6 eq) overnight. The resin was filtered, washed with DMF and DCM, and dried.

After deprotecting the Fmoc group by treatment of 20% PIP in DMF, the resin was washed with DMF. This resin was

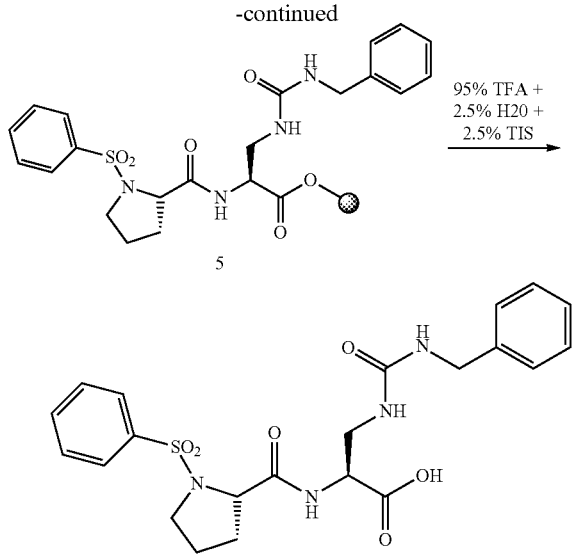

First, the 4-(Bromomethyl)phenoxymethyl polystyrene resin was swelled in DMF (10 mL/g resin). Fmoc-DAP(Alloc)-OH (1.5 eq), CsI (1.5 eq), and DIEA (2 eq) were added and the reaction was stirred at room temperature overnight. The resin was filtered and washed repeatedly with DMF (1*1 min, 1*10 min, 1*1 min) and MeOH (1*1 min, 1*10 min, 1*1 min).

Next, a solution of PhSiH$_3$ (24 eq) was added to a peptide resin washed with oxygen-free DCM in the presence of Argon, and the resin was stirred for 2 min. Subsequently, Pd (PPh$_3$)$_4$ (0.5 eq) was added under Argon. The reaction was stirred for 2 hr under Argon. Then, the resin was washed repeatedly with DCM (1*1 min, 1*10 min, 1*1 min) and DMF (1*1 min, 1*10 min, 1*1 min). This resin was then suspended with DMF and reacted with N-Benzyl-formamide (3 eq) and DIEA (6 eq) overnight.

After deprotecting the Fmoc group by treatment of 20% PIP in DMF, the resin was washed with DMF (1*1 min, 1*10 min, 3*1 min). The resin was then suspended with DMF and reacted with Fmoc-Pro-OH (3 eq), HATU (3 eq), HOAT (3 eq), and DIEA (6 eq) for 3 h. The resin was filtered and washed with DMF (1*1 min, 1*10 min, 3*1 min).

After deprotecting the remaining Fmoc group by treatment of 20% PIP in DMF, the resin was washed with DMF (1*1 min, 1*10 min, 3*1 min). This resin was then suspended with DCM and reacted with benzenesulfonyl chloride (3 eq) and DIEA (6 eq) overnight. The resin was filtered, washed with DCM (1*1 min, 1*10 min, 1*1 min) and DMF (1*1 min, 1*10 min, 1*1 min), and dried.

The 3-(3-Benzyl-ureido)-2-{[1-(4-nitro-benzenesulfonyl)-pyrrolidine-2-carbonyl]-amino}-propionic acid molecule, shown in Table 1 as Compound 20, was cleaved from the resin by treatment of 95% TFA, 2.5% TIS, and 2.5% water. Purification was carried on HPLC.

Example 8

Characterization of Compounds by Mass Spectrometry and NMR

Compounds were characterized by use of a VG Micromass 7070H high resolution chemical ionization mass spectrometer interfaced with a Kratos DS-50-S data system for mass spectrometry analysis, and with a Bruker drx-500 spectrometer for NMR characterization.

For example, Compound 20, as shown in Table 1, was characterized using the described equipment and yielded the following results: $^1$H NMR (500 MHz, DMSO-d$_6$): δ 1.42-1.48 (m, 1H), 1.55-1.62 (m, 1H), 1.67-1.75 (m, 1H), 1.77-1.82 (s, 1H), 3.13 (ddd, 1H), 3.32-3.38 (m, 1H), 3.40-3.50 (m, 2H), 4.12 (dd, 1H), 4.20 (d, 2H), 4.23 (ddd, 1H), 6.08 (t, 1H), 6.60 (t, 1H), 7.19-7.24 (m, 2H), 7.29 (t, 2H), 7.63 (t, 2H), 7.72 (t, 1H), 7.87 (d, 2H), 8.15 (d, 1H). 12.73 (br, 1H); EI-MS: m/z (M+Na$^+$): 497.147 (calc'd), 497.147 (found).

The other preferred embodiments were evaluated in like fashion. All characterizations confirmed the fidelity of the synthesis reactions described above and therefore the accuracy of the structural descriptions provided in Table 1.

Example 9

Platelet Adhesion Assay

The inhibitory strength of the compounds of the present disclosure was analyzed as against platelet adhesion to type I collagen. Ninety-six well flat bottom microtiter plates (Immulon 2, Dynatech Laboratories, Chantilly, Va.) were coated with collagen, purified human fibrinogen, or bovine serum albumin, each dissolved in 50 mM NaHCO$_3$ buffer, pH 8.0, containing 150 mM NaCl as previously described. See Bennett J S, Chan C, Vilaire G, Mousa S A, DeGrado W F. *Agonist-Activated αvβ3 on Platelets and Lymphocytes Binds to the Matrix Protein Osteopontin. J Biol Chem.* 272, 8137-814) (1997). Unoccupied protein binding sites on the wells were blocked with 5 mg/ml bovine serum albumin dissolved in the same buffer. Human platelets were isolated from blood anticoagulated with 0.1 volume 3.8% sodium citrate by gel-filtration using a 4 mM HEPES buffer, pH 7.4, containing 135 mM NaCl, 2.7 mM KCl, 5.6 mM glucose, 3.3 mM NaH$_2$PO$_4$, 0.35 mg/ml bovine serum albumin and various concentrations of CaCl$_2$ or MgCl$_2$ according to the experiment. One hundred μl aliquots of the gel-filtered platelet suspension containing 1-2×10$^8$ platelets were added to the protein-coated wells in the absence or presence of a platelet agonist. Following an incubation for 30 min at 37° C. without agitation, the plates were washed 4 times with the Tris-buffered NaCl, containing 2 mM MgCl$_2$, pH 7.4, and the number of adherent platelets measured using the colorimetric assay reported by Bellavite P, Andrioli G, Guzzo P, et al. *A colorimetric method for the measurement of platelet adhesion in microtiter plates. Anal Biochem.* 216, 444-450 (1994). Briefly, 150 μl of a 0.1 M citrate buffer, pH 5.4, containing 5 mM p-nitrophenyl phosphate and 0.1% Triton X-100 was added to the wells after washing. After an incubation for 60 min at room temperature in the absence of ambient light, color was developed by the addition of 100 μl of 2N NaOH and, using EL800 Universal Microplate Reader (Bio-Tek Instruments, Inc., Winooski, Vt.), read in microtiter plate reader at 405 nm.

The potencies of the compounds of the present disclosure were determined by testing the ability of a range of concentrations of each compound to inhibit human platelet adhesion to soluble collagen under static conditions. Owing to the fact that soluble collagen is a specific ligand for α2β1 integrin, this is an accepted method of assessing α2β1 inhibition on platelets. Accordingly, the reported IC$_{50}$ values represent the amount of compound required to reduce type I collagen-induced platelet adhesion by 50% (i.e., as demonstrated by the assay described in Example 9). While not intending to be bound by any theory or theories of operation, it is believed that these results suggest that the compounds of the present invention may effect inhibition of the 2β1 integrin by targeting the integrin's "I-like" domain.

$IC_{50}$ values were determined by using the platelets of a single donor. In cases where multiple assays were performed, the reported results reflect the average $IC_{50}$ value derived from the separate assays.

Compounds 1-53, which are preferred embodiments, are shown in Table 1.

TABLE 1

| Compound | Name | Structure | $IC_{50}$ (nM) |
|---|---|---|---|
| 1 | 3-tert-Butoxycarbonylamino-2-{[1-(4-nitro-benzenesulfonyl)-pyrrolidine-2-carbonyl]-amino}-propionic acid | 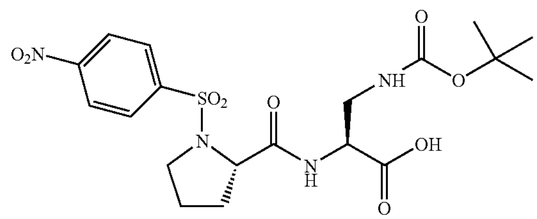 | $2.62 \times 10^3$ |
| 2 | 3-Benzyloxycarbonylamino-2-{[1-(4-nitro-benzenesulfonyl)-pyrrolidine-2-carbonyl]-amino}-propionic acid | 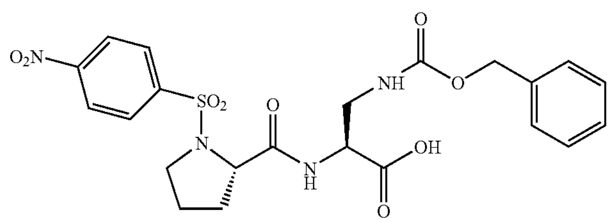 | $2.30 \times 10^3$ |
| 3 | 3-Benzoylamino-2-{[1-(4-nitro-benzenesulfonyl)-pyrrolidine-2-carbonyl]-amino}-propionic acid | 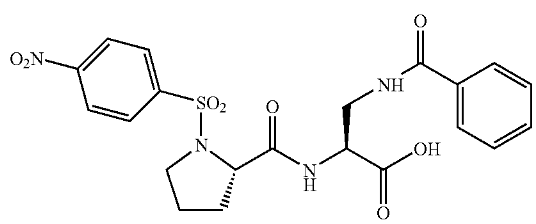 | $2.31 \times 10^3$ |
| 4 | 2-{[1-(4-Nitro-benzenesulfonyl)-pyrrolidine-2-carbonyl]-amino}-3-(3-phenyl-propionylamino)-propionic acid | 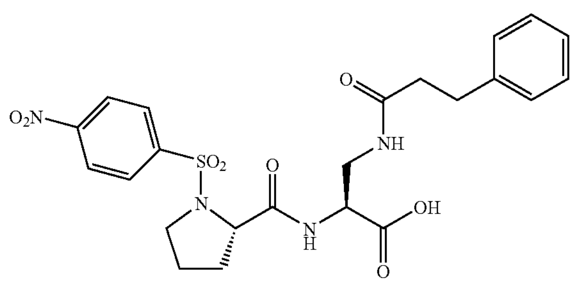 | $4.75 \times 10^3$ |
| 5 | 3-(3-Benzyl-ureido)-2-{[1-(4-nitro-benzenesulfonyl)-pyrrolidine-2-carbonyl]-amino}-propionic acid | 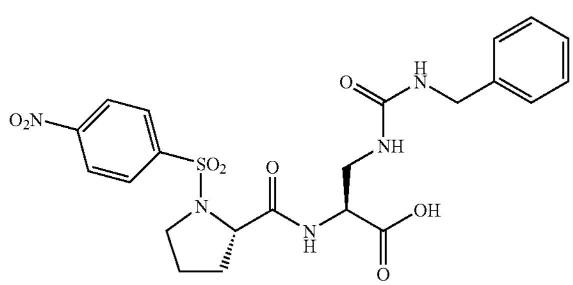 | $1.05 \times 10^2$ |

TABLE 1-continued

| Compound | Name | Structure | IC$_{50}$ (nM) |
|---|---|---|---|
| 6 | 2-{[1-(4-Nitro-benzenesulfonyl)-pyrrolidine-2-carbonyl]-amino}-pentanedioic acid 5-tert-butyl ester | 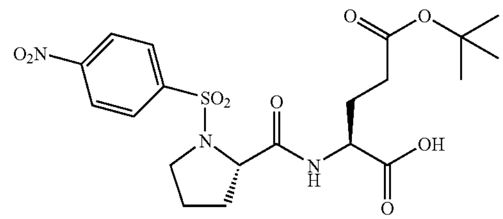 | $2.23 \times 10^4$ |
| 7 | 3-[3-(2-Chloro-benzyl)-ureido]-2-{[1-(4-nitro-benzenesulfonyl)-pyrrolidine-2-carbonyl]-amino}-propionic acid | 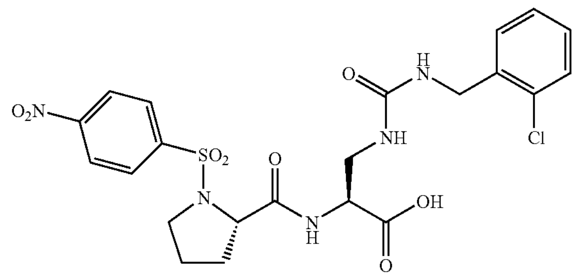 | $9.85 \times 10^2$ |
| 8 | 3-[3-(4-Bromo-benzyl)-ureido]-2-{[1-(4-nitro-benzenesulfonyl)-pyrrolidine-2-carbonyl]-amino}-propionic acid | 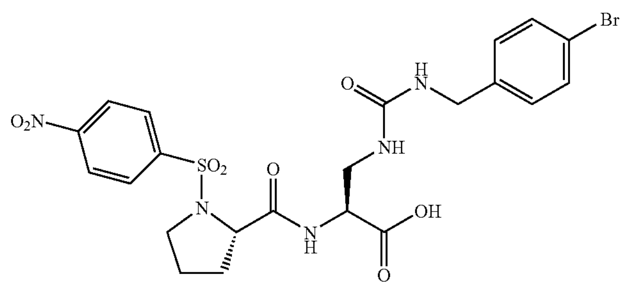 | $1.62 \times 10^3$ |
| 9 | 2-{[1-(4-Nitro-benzenesulfonyl)-pyrrolidine-2-carbonyl]-amino}-3-(3-phenyl-ureido)-propionic acid | 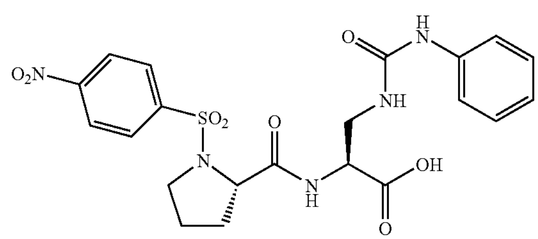 | $3.00 \times 10^3$ |
| 10 | 2-{[1-(4-Nitro-benzenesulfonyl)-pyrrolidine-2-carbonyl]-amino}-3-[3-(4-nitro-phenyl)-ureido]-propionic acid | 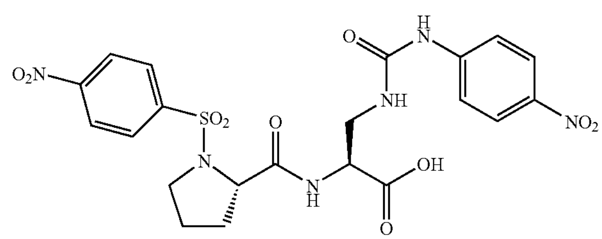 | $4.60 \times 10^3$ |
| 11 | 3-(3-Biphenyl-4-yl-ureido)-2-{[1-(4-nitro-benzenesulfonyl)-pyrrolidine-2-carbonyl]-amino}-propionic acid | 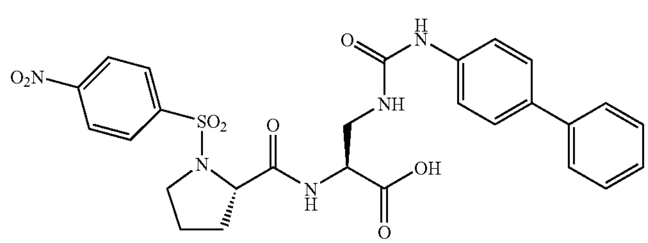 | $5.06 \times 10^3$ |

TABLE 1-continued

| Compound | Name | Structure | IC$_{50}$ (nM) |
|---|---|---|---|
| 12 | 3-[3-(4-Methoxy-benzyl)-ureido]-2-{[1-(4-nitro-benzenesulfonyl)-pyrrolidine-2-carbonyl]-amino}-propionic acid | 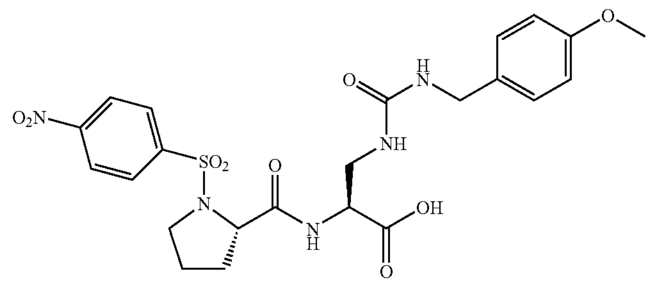 | $8.10 \times 10^2$ |
| 13 | 3-[3-(2-Methoxy-benzyl)-ureido]-2-{[1-(4-nitro-benzenesulfonyl)-pyrrolidine-2-carbonyl]-amino}-propionic acid | 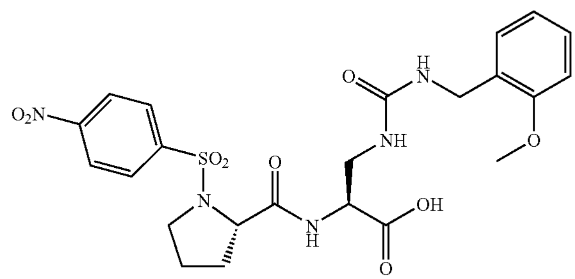 | $1.5 \times 10^3$ |
| 14 | 3-[3-(3-Methoxy-benzyl)-ureido]-2-{[1-(4-nitro-benzenesulfonyl)-pyrrolidine-2-carbonyl]-amino}-propionic acid | 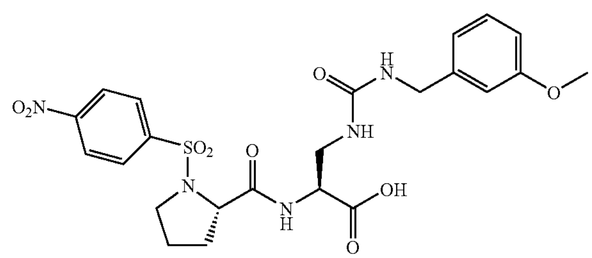 | $7.90 \times 10^2$ |
| 15 | 3-(3-Biphenyl-4-ylmethyl-ureido)-2-{[1-(4-nitro-benzenesulfonyl)-pyrrolidine-2-carbonyl]-amino}-propionic acid | 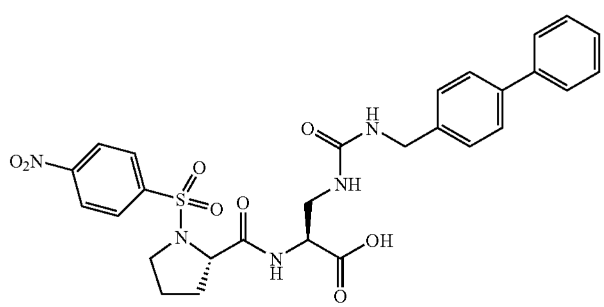 | $4.10 \times 10^3$ |
| 16 | 2-{[1-(4-Nitro-benzenesulfonyl)-pyrrolidine-2-carbonyl]-amino}-3-(3-propyl-ureido)-propionic acid | 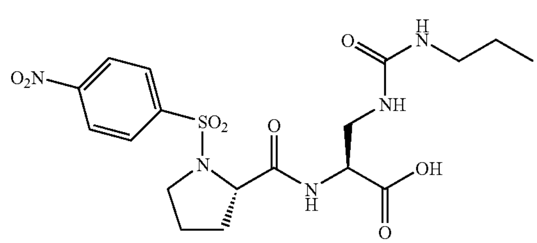 | $3.60 \times 10^3$ |

TABLE 1-continued

| Compound | Name | Structure | IC$_{50}$ (nM) |
|---|---|---|---|
| 17 | 3-(3-tert-Butyl-ureido)-2-{[1-(4-nitro-benzenesulfonyl)-pyrrolidine-2-carbonyl]-amino}-propionic acid | 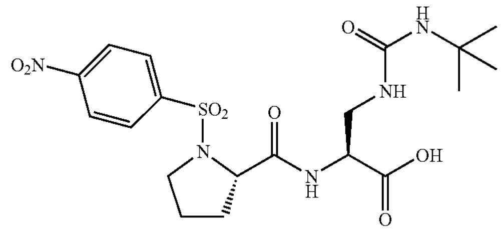 | $1.70 \times 10^3$ |
| 18 | 3-[3-(4-tert-Butoxycarbonylamino-benzyl)-ureido]-2-{[1-(4-nitro-benzenesulfonyl)-pyrrolidine-2-carbonyl]-amino}-propionic acid | 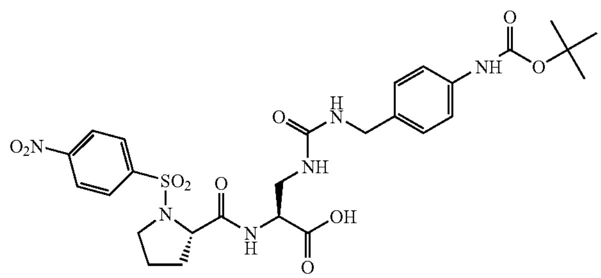 | $1.77 \times 10^3$ |
| 19 | 3-[3-(4-Amino-benzyl)-ureido]-2-{[1-(4-nitro-benzenesulfonyl)-pyrrolidine-2-carbonyl]-amino}-propionic acid | 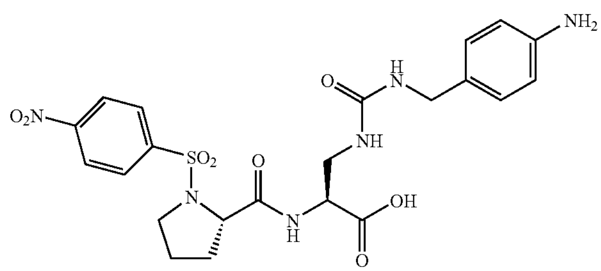 | $4.6 \times 10^2$ |
| 20 | 2-[(1-Benzenesulfonyl-pyrrolidine-2-carbonyl)-amino]-3-(3-benzyl-ureido)-propionic acid | 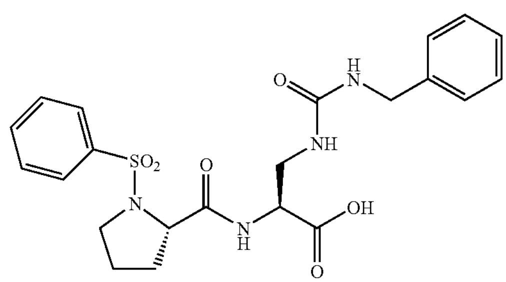 | $1.50 \times 10^1$ |
| 21 | 2-{[1-(4-Acetylamino-benzenesulfonyl)-pyrrolidine-2-carbonyl]-amino}-3-(3-benzyl-ureido)-propionic acid | 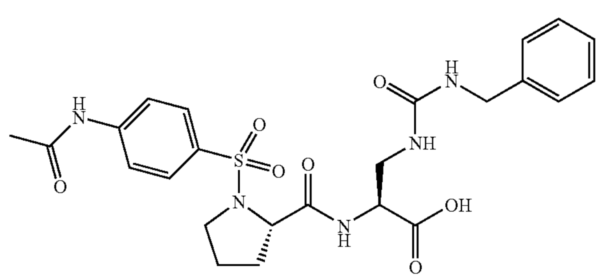 | $1.31 \times 10^2$ |

TABLE 1-continued

| Compound | Name | Structure | IC$_{50}$ (nM) |
|---|---|---|---|
| 22 | 3-(3-Benzyl-ureido)-2-[(1-phenylmethanesulfonyl-pyrrolidine-2-carbonyl)-amino]-propionic acid | 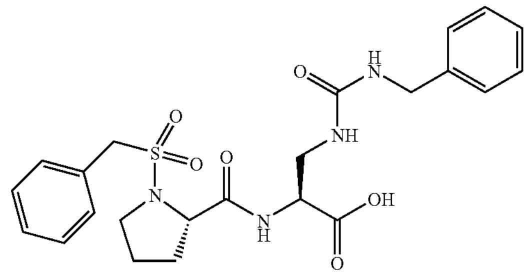 | $1.17 \times 10^4$ |
| 23 | 2-[2-(3-Benzyl-ureido)-1-carboxy-ethylcarbarmoyl]-pyrrolidine-1-carboxylic acid benzyl ester | 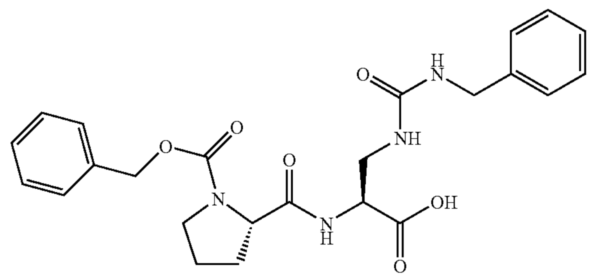 | $2.80 \times 10^4$ |
| 24 | 3-(3-Benzyl-ureido)-2-{[1-(biphenyl-4-sulfonyl)-pyrrolidine-2-carbonyl]-amino}-propionic acid | 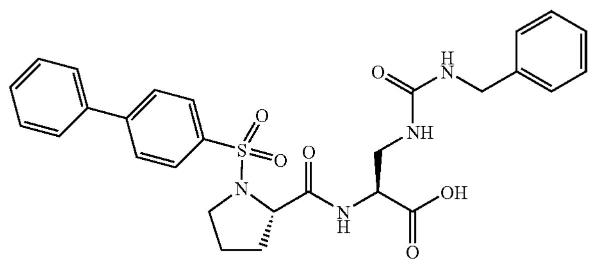 | $2.87 \times 10^2$ |
| 25 | 2-{[1-(4-Amino-benzenesulfonyl)-pyrrolidine-2-carbonyl]-amino}-3-(3-benzyl-ureido)-propionic acid | 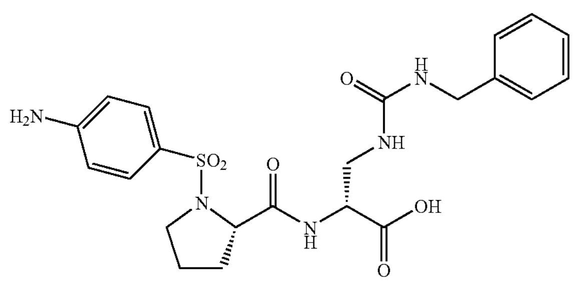 | $2.03 \times 10^3$ |
| 26 | 2-[(1-Benzoyl-pyrrolidine-2-carbonyl)-amino]-3-(3-benzyl-ureido)-propionic acid | 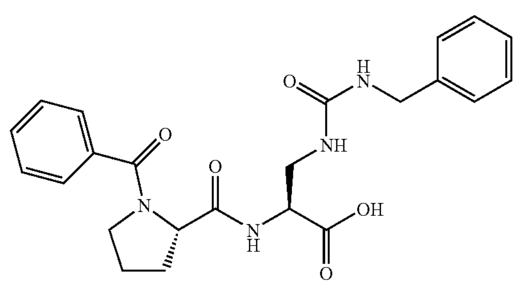 | $1.00 \times 10^6$ |

TABLE 1-continued

| Compound | Name | Structure | IC$_{50}$ (nM) |
|---|---|---|---|
| 27 | 3-(3-Benzyl-ureido)-2-{[1-(toluene-4-sulfonyl)-pyrrolidine-2-carbonyl]-amino}-propionic acid | 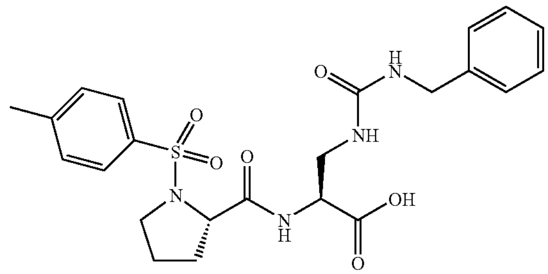 | $3.60 \times 10^1$ |
| 28 | 3-(3-Benzyl-ureido)-2-{[1-naphthalene-1-sulfonyl)-pyrrolidine-2-carbonyl]-amino}-propionic acid | 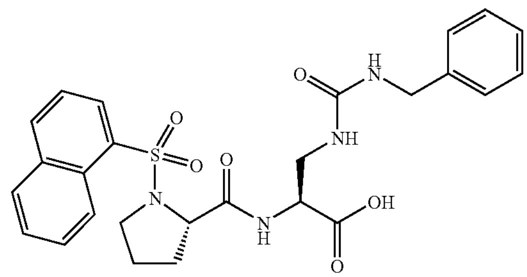 | $1.94 \times 10^3$ |
| 29 | 3-(3-Benzyl-ureido)-2-{[1-naphthalene-2-sulfonyl)-pyrrolidine-2-carbonyl]-amino}-propionic acid | 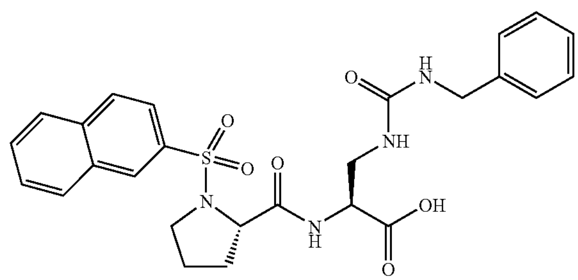 | $9.00 \times 10^2$ |
| 30 | 3-[3-(4-Amino-benzyl)-ureido]-2-[(1-benzenesulfonyl-pyrrolidine-2-carbonyl)-amino]-propionic acid | 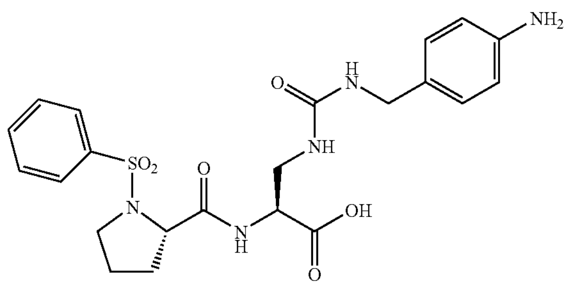 | $2.30 \times 10^1$ |
| 31 | 3-(3-Benzyl-ureido)-2-{[1-(3,5-dimethyl-benzenesulfonyl)-pyrrolidine-2-carbonyl]-amino}-propionic acid | 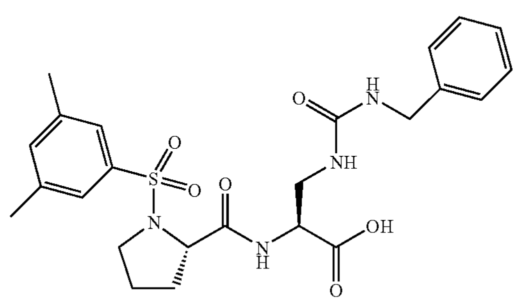 | $2.90 \times 10^1$ |

TABLE 1-continued

| Compound | Name | Structure | IC$_{50}$ (nM) |
|---|---|---|---|
| 32 | 3-(3-Benzyl-ureido)-2-{[1-(4-phenylacetylamino-benzenesulfonyl)-pyrrolidine-2-carbonyl]-amino}-propionic acid | 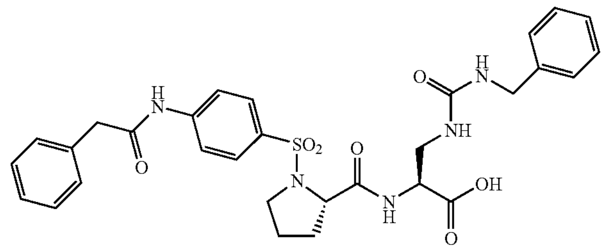 | $2.36 \times 10^2$ |
| 33 | 3-(3-Benzyl-ureido)-2-({1-[4-(3-phenyl-ureido)-benzenesulfonyl]-pyrrolidine-2-carbonyl}-amino)-propionic acid | 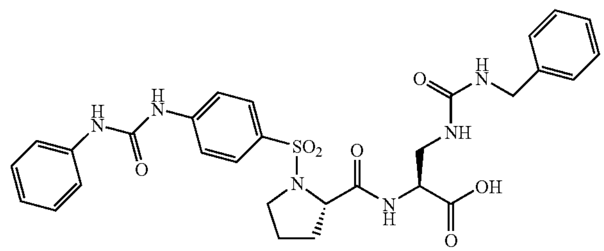 | $1.51 \times 10^2$ |
| 34 | 3-(3-Benzyl-ureido)-2-{[1-(naphthalene-2-sulfonyl)-pyrrolidine-2-carbonyl]-amino}-propionic acid | 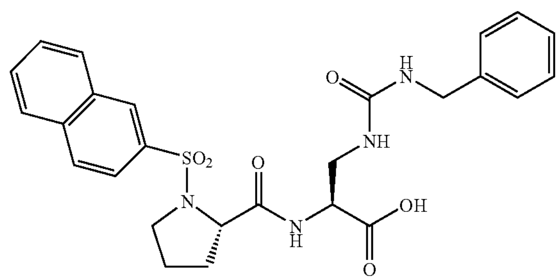 | $5.00 \times 10^1$ |
| 35 | 2-[(1-Benzenesulfonyl-pyrrolidine-2-carbonyl)-amino]-3-[3-(2-chloro-benzyl)-ureido]-propionic acid | 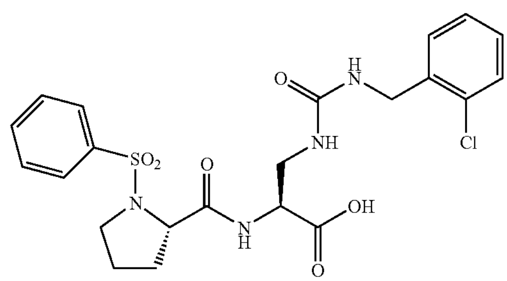 | $1.07 \times 10^2$ |
| 36 | 2-[(1-Benzenesulfonyl-pyrrolidine-2-carbonyl)-amino]-3-(3-phenyl-ureido)-propionic acid | 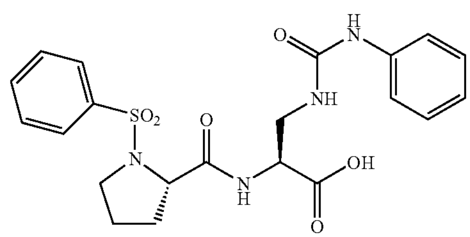 | $2.96 \times 10^2$ |
| 37 | 2-[(1-Benzenesulfonyl-pyrrolidine-2-carbonyl)-amino]-3-(3-phenyl-propionylamino)-propionic acid | 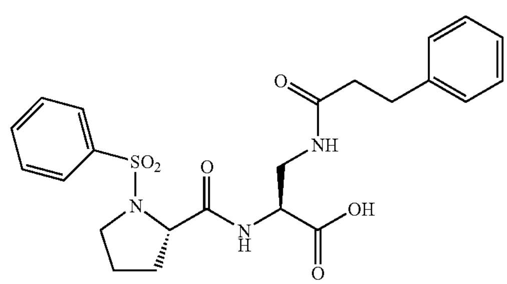 | $3.67 \times 10^2$ |

TABLE 1-continued

| Compound | Name | Structure | IC$_{50}$ (nM) |
|---|---|---|---|
| 38 | 2-[(1-Benzenesulfonyl-pyrrolidine-2-carbonyl)-amino]-3-benzoylamino-propionic acid | 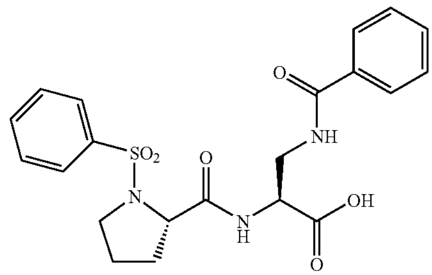 | $6.60 \times 10^2$ |
| 39 | 2-[(1-Benzenesulfonyl-pyrrolidine-2-carbonyl)-amino]-3-benzyloxycarbonylamino-propionic acid | 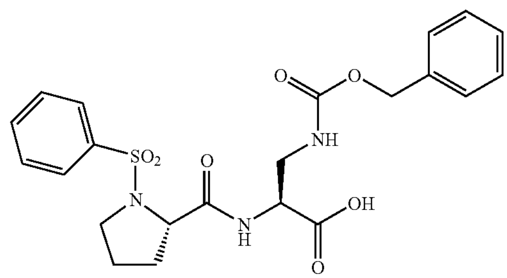 | $1.85 \times 10^2$ |
| 40 | 2-[(1-Benzenesulfonyl-pyrrolidine-2-carbonyl)-amino]-3-[3-(2-methoxy-benzyl)-ureido]-propionic acid | 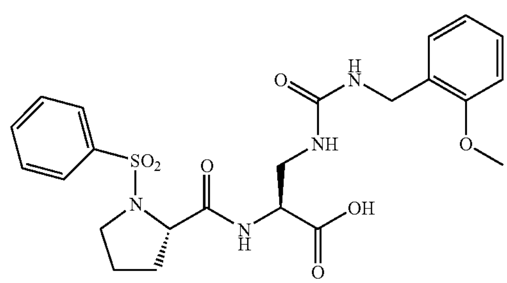 | $4.67 \times 10^2$ |
| 41 | 2-[(1-Benzenesulfonyl-pyrrolidine-2-carbonyl)-amino]-3-[3-(3-methoxy-benzyl)-ureido]-propionic acid | 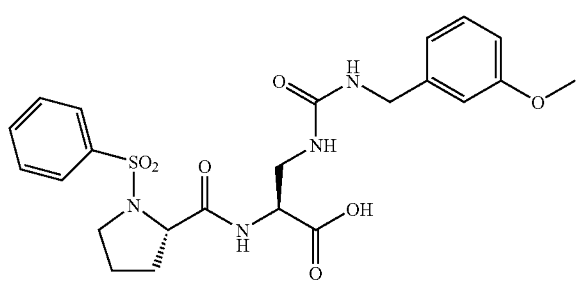 | $1.60 \times 10^2$ |
| 42 | 2-[(1-Benzenesulfonyl-pyrrolidine-2-carbonyl)-amino]-3-{3-propyl-ureido)-propionic acid | 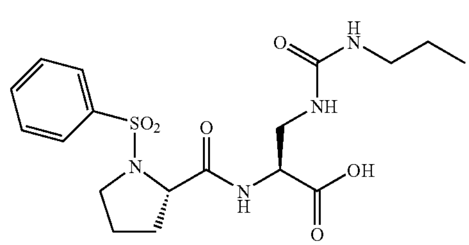 | $3.67 \times 10^2$ |

TABLE 1-continued

| Compound | Name | Structure | IC$_{50}$ (nM) |
|---|---|---|---|
| 43 | 3-(3-Benzyl-ureido)-2-{[1-(3,5-difluoro-benzenesulfonyl)-pyrrolidine-2-carbonyl]-amino}-propionic acid | 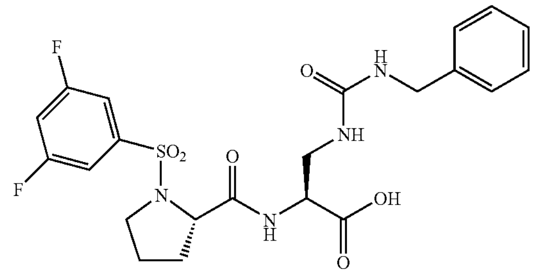 | $3.50 \times 10^1$ |
| 44 | 3-(3-Benzyl-ureido)-2-{[1-(4-methanesulfonyl-benzenesulfonyl)-pyrrolidine-2-carbonyl]-amino}-propionic acid | 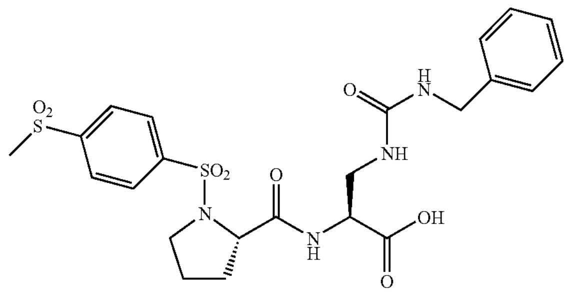 | $7.0 \times 10^1$ |
| 45 | 2-[(1-Benzenesulfonyl-pyrrolidine-2-carbonyl)-amino]-3-(3-tert-butyl-ureido)-propionic acid | 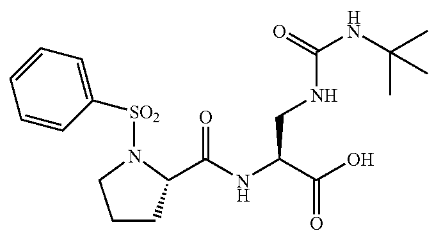 | $1.85 \times 10^2$ |
| 46 | 2-[(1-Benzenesulfonyl-4-benzyloxy-pyrrolidine-2-carbonyl)-amino]-3-(3-benzyl-ureido)-propionic acid | 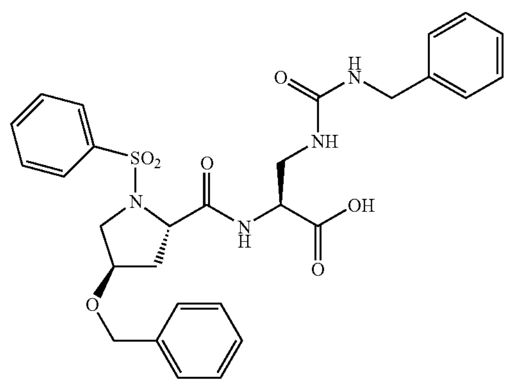 | $2.40 \times 10^2$ |
| 47 | 2-[(1-Benzenesulfonyl-4-hydroxy-pyrrolidine-2-carbonyl)-amino]-3-(3-benzyl-ureido)-propionic acid | 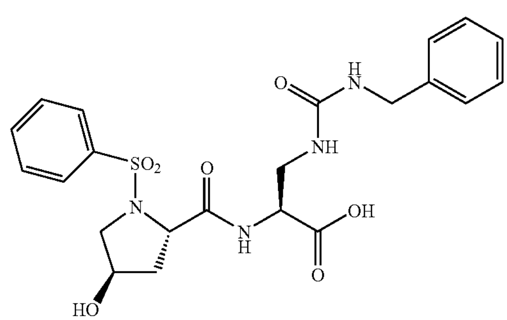 | $3.40 \times 10^1$ |

TABLE 1-continued

| Compound | Name | Structure | IC$_{50}$ (nM) |
|---|---|---|---|
| 48 | 3-(3-Benzyl-ureido)-2-{[1-(3,5-dichloro-benzenesulfonyl)-pyrrolidine-2-carbonyl]-amino}-propionic acid | 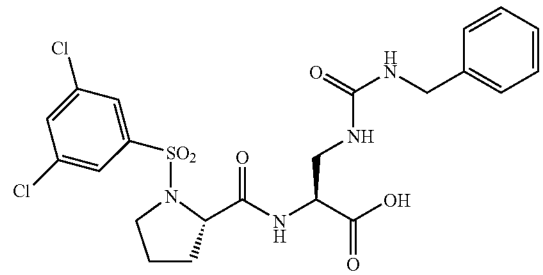 | $1.70 \times 10^1$ |
| 49 | 3-(3-Benzyl-ureido)-2-{[1-(3,5-bis-trifluoromethyl-benzenesulfonyl)-pyrrolidine-2-carbonyl]-amino}-propionic acid | 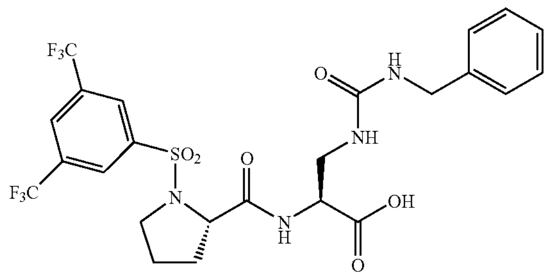 | $3.90 \times 10^1$ |
| 50 | 2-[(3-Benzenesulfonyl-5,5-dimethyl-thiazolidine-4-carbonyl)-amino]-3-(3-benzyl-ureido)-propionic acid | 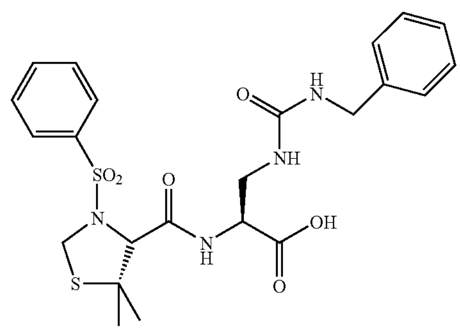 | $2.40 \times 10^1$ |
| 51 | 2-[(1-Benzenesulfonyl-piperidine-2-carbonyl)-amino]-3-(3-benzyl-ureido)-propionic acid | 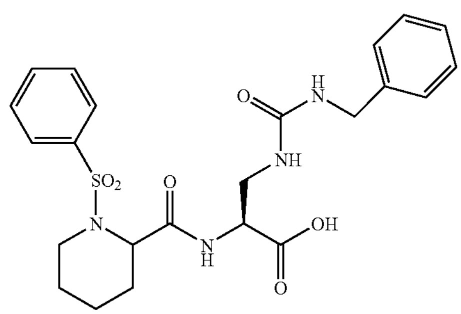 | $5.6 \times 10^1$ |
| 52 | 2-[(1-Benzenesulfonyl-2,5-dihydro-1H-pyrrole-2-carbonyl)-amino]-3-(3-benzyl-ureido)-propionic acid | 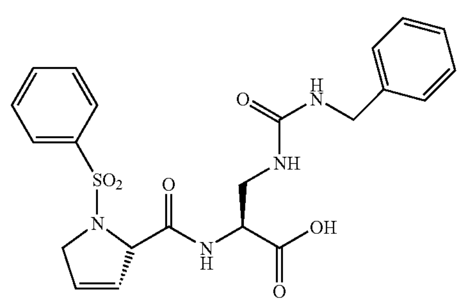 | $1.43 \times 10^2$ |

TABLE 1-continued

| Compound | Name | Structure | $IC_{50}$ (nM) |
|---|---|---|---|
| 53 | 2-[(1-Benzenesulfonyl-pyrrolidine-2-carbonyl)-amino]-3-(3-benzyl-ureido)-propionic acid | 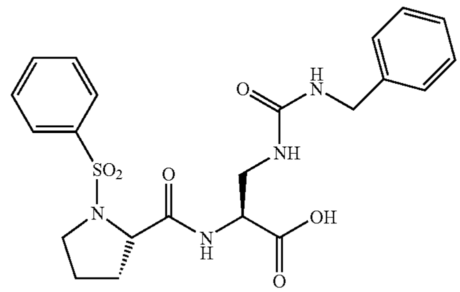 | $5.8 \times 10^1$ |

Compounds 1-53, listed in Table 1, were tested in vitro for their ability to inhibit the adhesion of platelets in the presence of type I (monomeric) collagen. These compounds were found to exhibit potent inhibitory activity. For example, Compound 20 was found to possess potent in vitro activity ($IC_{50}=15$ nM). Compound 30 was also found to possess potent in vitro inhibitory activity ($IC_{50}=23$ nM), as were Compound 31 ($IC_{50}=29$ nM) and Compound 48 ($IC_{50}=17$ nM).

Example 10

In Vivo Assay

To assess the in vivo activity of the inventive compounds as compared with an untreated arterial injury, carotid artery thrombi were simulated and subjected to test treatment. Ferric chloride-induced arterial injury was performed according to published protocol See Kufrin, D., et al., *Antithrombotic thrombocytes: ectopic expression of urokinase-type plasminogen activator in platelets. Blood.* 102 (3):926-933 (2003). The right common carotid artery was exposed by blunt dissection and the test subject mouse was dosed intravenously with compound 20 (30 mg/kg, 40 mM HEPES and 150 mM NaCl) (see Table 1, supra). The exposed carotid artery was positioned onto a miniature Doppler flow probe (Model 0.5VB; Transonic Systems, Ithaca, N.Y.). A 1.0×2 mm² strip of No. 1 Whatman filter paper soaked in 20% $FeCl_3$ was then applied to the adventitial surface of the artery for 2 minutes. The blood flow was monitored for 30 minutes. The amount of elapsed time to achieve initial occlusion in a control subject, in the presence of aspirin, and in the presence of compound were monitored, respectively. Results are provided in Table 2, below.

TABLE 2

| | Control | Compound | Aspirin |
|---|---|---|---|
| 1 | 3.35* | 6.92 | 6.25 |
| 2 | 6.69 | 6.02 | 8.03 |

TABLE 2-continued

| | Control | Compound | Aspirin |
|---|---|---|---|
| 3 | 5.87 | 8.25 | 6.69 |
| 4 | 5.8 | 6.69 | 6.5 |
| 5 | 6.42 | 5.8 | 7 |
| 6 | — | 6.69 | — |
| Average | 5.63 | 6.73 | 6.89 |

*Numbers provided signify time (seconds) elapsed to initial occlusion

Example 11

Cell Adhesion Assay to Assess Specificity

The ligands (3 µg/ml of collagen IV for α2β1 or 3 µg/ml of collagen I for α2β1) for the test designed to assess the specificity of representative embodiments of the instant compounds for the α2β1 integrin were immobilized on 96-well flat microtiter plates (100 µl for each well) in PBS buffer solution overnight at 4° C. In the case of VCAM (3 µg/ml, for α4β1) and fibronectin (10 µg/ml, for α5β1), 20 mM acetic acid was used instead of PBS buffer solution. As those skilled in the art will recognize, VCAM is a known endothelial ligand for α4β1/VLA-4, and fibronectin is a known ligand for α4β1/VLA-5. In the case of α1β1 and α2β1, blocking was performed with 1% BSA in HBSS buffer solution containing $Mg^{2+}$ (but without $Ca^{2+}$) for 1 hour. In the case of α4β1 and α5β1, 1% BSA in HyQ HBSS buffer solution containing $Ca^{2+}$ and $Mg^{2+}$ was used. Cells in the same buffer solution without BSA were labeled with incubation of 12.5 µM CMFDA at 37° C. for 30 minutes. After centrifugation and washing with buffer solution containing 1% BSA, cells were re-suspended in same buffer solution ($1 \times 10^6$ cells/ml) and incubated in the presence of a different concentration of inhibitors at room temperature for 15 minutes. Cells were added to the wells (100 µl/well) and incubated at 37° C. for 30 minutes. Unbound cells were washed out and bound cells were lysed by the addition of 0.5% Triton X-100.

The K562 cells expressing α5β1 integrin, Jurkat cells expressing α4β1, and K562 cells transfected with α1 and α2 integrins were provided by Dr. C. Marcinkiewicz (Temple University, Philadelphia, Pa.).

Plates were read using a Cytofluor 2350 fluorescence plate reader (Millipore, Bedford, Mass.) with a 485 nm (excitation) and 530 nm (emission). Results are provided below in Table 3.

TABLE 3

| Integrin | Cell line | Ligand | Compound[‡] 20 | 29 | 30 IC$_{50}$ (nM) | 31 | 48 |
|---|---|---|---|---|---|---|---|
| α2β1 | Platelet | Collagen I | 15 | 50 | 23 | 29 | 17 |
| α1β1[†] | K562* | Collagen IV | 29% | 30% | 22% | 26% | 32% |
| α2β1 | K562* | Collagen I | 138 | 177 | 102 | 89 | 83 |
| α4β1 | Jurkat | VCAM | 2128 | 4334 | 1966 | 740 | 637 |
| α5β1 | K562 | Fibronectin | >1 × 10$^4$ | >1 × 10$^4$ | >1 × 10$^4$ | >1 × 10$^4$ | >1 × 10$^4$ |

[†]Results displayed in terms of % inhibition at 3 μM
*Transfected K562 Cell
[‡]See Table 1

The tested compounds were found to display potent inhibitory activity between platelets and type I (monomeric) collagen, as well as between α2β1-transfected K562 cells and type I collagen. In contrast, minimal inhibition was achieved between α1β1-transfected K562 cells and type IV collagen, a recognized ligand for α1β1; between α4β1-expressing Jurkat cells and VCAM, a recognized ligand for α4β1; and between α5β1-expressing K562 cells and fibronectin, a known ligand for α5β1. Specificity of the tested compounds for the α2β1 integrin, as compared with related integrins, was thereby demonstrated.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound having the formula:

wherein:
R$^0$ is methylene;
R$^1$ is NH(aralkyl), NHSO$_2$aryl, NHSO$_2$alkyl, CH$_2$C(=O)alkoxy, NHC(=O)R$^2$, or NHSO$_2$R$^2$;
R$^2$ is aryl, alkyl, alkoxy, aralkyl, aralkoxy, aralkylamino, arylamino, or alkylamino;
Each R$^3$ is independently halo, nitro, aryl, amino, alkyl, alkoxy, NH-Boc, alkylsulfonyl, NHC(=O)alkyl, NHC(=O)aralkyl, or NHC(=O)arylamino;
Each R$^4$ is independently amino, hydroxy, aralkoxy, NH(aryl), or NHC(=O)aryl;
R$^5$ is H or alkyl;
R$^6$ is H or =O;
A is SO$_2$, PO$_2$, or C=O;
D is optional and may be one or more CH$_2$ groups;
E is aryl or heteroaryl;
n is 0, 1, or 2;
m is 0 or 1;
one of the three dashed-line portions may represent a double bond, and,
q is 0, 1, 2, or 3;
or a stereoisomer, partial stereoisomer, pharmaceutically acceptable salt, acid hydrate, or N-oxide thereof.

2. The compound according to claim 1, wherein:
R$^1$ is NH(aralkyl), NHSO$_2$aryl, CH$_2$C(=O)alkoxy, or NHC(=O)aralkoxy;
Each R$^4$ is independently hydroxy or aralkoxy;
A is SO$_2$, or C=O; and,
E is aryl;
or a stereoisomer, partial stereoisomer, pharmaceutically acceptable salt, acid hydrate, or N-oxide thereof.

3. A composition comprising a compound according to claim 1 and a pharmaceutically acceptable carrier, diluent, or excipient.

4. A composition comprising a stereochemically enriched mixture of compounds according to claim 1.

5. The compound according to claim 1, where A is C=O and E is phenyl.

6. The compound according to claim 1, where A is SO$_2$.

7. The compound according to claim 6, where E is phenyl and D represents a bond between A and E.

8. The compound according to claim 7, where n equals 0.

9. The compound according to claim 7, where n=1.

10. The compound according to claim 9, where R$^3$ is amino, acetamino, nitro, methyl, phenyl, benzyl, NHC(=O)benzyl, NHC(=O)phenylamino, or methylsulfonyl.

11. The compound according to claim 10, where R$^1$ is NH(aralkyl), NHSO$_2$aryl, CH$_2$C(=O)alkoxy, or NHC(=O)aralkoxy.

12. The compound according to claim 9, wherein R$^3$ is nitro and R$^1$ is —NH(aralkyl), —NHSO$_2$aryl, CH$_2$C(=O)alkoxy, or —NHC(=O)aralkoxy.

13. The compound according to claim 7, where n=2.

14. The compound according to claim 13, wherein R$^3$ is alkyl or halo, R$^1$ is NH(aralkyl), NHSO$_2$aryl, CH$_2$C(=O)alkoxy, or NHC(=O)aralkoxy.

15. The compound according to claim 1, wherein the compound is:
3-tert-Butoxycarbonylamino-2-{[1-(4-nitro-benzenesulfonyl)-pyrrolidine-2-carbonyl]-amino}-propionic acid;
3-Benzyloxycarbonylamino-2-{[1-(4-nitro-benzenesulfonyl)-pyrrolidine-2-carbonyl]-amino}-propionic acid;

3-Benzoylamino-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-3-(3-phenyl-propionylamino)-propionic acid;
3-(3-Benzylamino)-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-pentanedioic acid 5-tert-butyl ester;
3-[3-(2-Chloro-benzyl)-ureido]-2-{[1-(4-nitro-benzenesulfonyl)-pyrrolidine-2-carbonyl]-amino}-propionic acid;
3-[3-(4-Bromo-benzyl)-ureido]-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-3-(3-phenyl-ureido)-propionic acid;
2-{[1-(4-Nitro-benzenesulfonyl)-pyrrolidine-2-carbonyl]-amino}-3-[3-(4-nitro-phenyl)-ureido]-propionic acid;
3-(3-Biphenyl-4-yl-ureido)-2-{[1-(4-nitro-benzenesulfonyl)-pyrrolidine-2-carbonyl]-amino}-propionic acid;
3-[3-(4-Methoxy-benzyl)-ureido]-2-{[1-(4-nitro-benzenesulfonyl)-pyrrolidine-2-carbonyl]-amino}-propionic acid;
3-[3-(2-Methoxy-benzyl)-ureido]-2-{[1-(4-nitro-benzenesulfonyl)-pyrrolidine-2-carbonyl]-amino}-propionic acid;
3-[3-(3-Methoxy-benzyl)-ureido]-2-{[1-(4-nitro-benzenesulfonyl)-pyrrolidine-2-carbonyl]-amino}-propionic acid;
3-(3-Biphenyl-4-ylmethyl-ureido)-2-{[1-(4-nitro-benzenesulfonyl)-pyrrolidine-2-carbonyl]-amino}-propionic acid;
2-{[1-(4-Nitro-benzenesulfonyl)-pyrrolidine-2-carbonyl]-amino}-3-(3-propyl-ureido)-propionic acid;
3-(3-tert-Butyl-ureido)-2-{[1-(4-nitro-benzenesulfonyl)-pyrrolidine-2-carbonyl]-amino}-propionic acid;
3-[3-(4-tert-Butoxycarbonylamino-benzyl)-ureido]-2-{[1-(4-nitro-benzenesulfonyl)-pyrrolidine-2-carbonyl]-amino}-propionic acid;
3-[3-(4-Amino-benzyl)-ureido]-2-{[1-(4-nitro-benzenesulfonyl)-pyrrolidine-2-carbonyl]-amino}-propionic acid;
2-[(1-Benzenesulfonyl-pyrrolidine-2-carbonyl)-amino]-3-(3-benzyl-ureido)-propionic acid;
2-{[1-(4-Acetylamino-benzenesulfonyl)-pyrrolidine-2-carbonyl]-amino}-3-(3-benzyl-ureido)-propionic acid;
3-(3-Benzyl-ureido)-2-[(1-phenylmethanesulfonyl-pyrrolidine-2-carbonyl)-amino]-propionic acid;
2-[2-(3-Benzyl-ureido)-1-carboxy-ethylcarbamoyl]-pyrrolidine-1-carboxylic acid benzyl ester;
3-(3-Benzyl-ureido)-2-{[1-(biphenyl-4-sulfonyl)-pyrrolidine-2-carbonyl]-amino}-propionic acid;
2-{[1-(4-Amino-benzenesulfonyl)-pyrrolidine-2-carbonyl]-amino}-3-(3-benzyl-ureido)-propionic acid;
2-[(1-Benzoyl-pyrrolidine-2-carbonyl)-amino]-3-(3-benzyl-ureido)-propionic acid;
3-(3-Benzyl-ureido)-2-{[1-(toluene-4-sulfonyl)-pyrrolidine-2-carbonyl]-amino}-propionic acid;
3-(3-Benzyl-ureido)-2-{[1-(naphthalene-1-sulfonyl)-pyrrolidine-2-carbonyl]-amino}-propionic acid;
3-(3-Benzyl-ureido)-2-{[1-(naphthalene-2-sulfonyl)-pyrrolidine-2-carbonyl]-amino}-propionic acid;
3-[3-(4-Amino-benzyl)-ureido]-2-[(1-benzenesulfonyl-pyrrolidine-2-carbonyl)-amino]-propionic acid;
3-(3-Benzyl-ureido)-2-{[1-(3,5-dimethyl-benzenesulfonyl)-pyrrolidine-2-carbonyl]-amino}-propionic acid;
3-(3-Benzyl-ureido)-2-{[1-(4-phenylacetylamino-benzenesulfonyl)-pyrrolidine-2-carbonyl]-amino}-propionic acid;
3-(3-Benzyl-ureido)-2-({1-[4-(3-phenyl-ureido)-benzenesulfonyl]-pyrrolidine-2-carbonyl}-amino)-propionic acid;
3-(3-Benzyl-ureido)-2-{[1-(naphthalene-2-sulfonyl)-pyrrolidine-2-carbonyl]-amino}-propionic acid;
2-[(1-Benzenesulfonyl-pyrrolidine-2-carbonyl)-amino]-3-[3-(2-chloro-benzyl)-ureido]-propionic acid;
2-[(1-Benzenesulfonyl-pyrrolidine-2-carbonyl)-amino]-3-(3-phenyl-ureido)-propionic acid;
2-[(1-Benzenesulfonyl-pyrrolidine-2-carbonyl)-amino]-3-(3-phenyl-propionylamino)-propionic acid;
2-[(1-Benzenesulfonyl-pyrrolidine-2-carbonyl)-amino]-3-benzoylamino-propionic acid;
2-[(1-Benzenesulfonyl-pyrrolidine-2-carbonyl)-amino]-3-benzyloxycarbonylamino-propionic acid;
2-[(1-Benzenesulfonyl-pyrrolidine-2-carbonyl)-amino]-3-[3-(2-methoxy-benzyl)-ureido]-propionic acid;
2-[(1-Benzenesulfonyl-pyrrolidine-2-carbonyl)-amino]-3-[3-(3-methoxy-benzyl)-ureido]-propionic acid;
2-[(1-Benzenesulfonyl-pyrrolidine-2-carbonyl)-amino]-3-(3-propyl-ureido)-propionic acid;
3-(3-Benzyl-ureido)-2-{[1-(3,5-difluoro-benzenesulfonyl)-pyrrolidine-2-carbonyl]-amino}-propionic acid;
3-(3-Benzyl-ureido)-2-{[1-(4-methanesulfonyl-benzenesulfonyl)-pyrrolidine-2-carbonyl]-amino}-propionic acid;
2-[(1-Benzenesulfonyl-pyrrolidine-2-carbonyl)-amino]-3-(3-tert-butyl-ureido)-propionic acid;
2-[(1-Benzenesulfonyl-4-benzyloxy-pyrrolidine-2-carbonyl)-amino]-3-(3-benzyl-ureido)-propionic acid;
2-[(1-Benzenesulfonyl-4-hydroxy-pyrrolidine-2-carbonyl)-amino]-3-(3-benzyl-ureido)-propionic acid;
3-(3-Benzyl-ureido)-2-{[1-(3,5-dichloro-benzenesulfonyl)-pyrrolidine-2-carbonyl]-amino}-propionic acid;
3-(3-Benzyl-ureido)-2-{[1-(3,5-bis-trifluoromethyl-benzenesulfonyl)-pyrrolidine-2-carbonyl]-amino}-propionic acid;
2-[(1-Benzenesulfonyl-piperidine-2-carbonyl)-amino]-3-(3-benzyl-ureido)-propionic acid;
2-[(1-Benzenesulfonyl-2,5-dihydro-1H-pyrrole-2-carbonyl)-amino]-3-(3-benzyl-ureido)-propionic acid; or,
2-[(1-Benzenesulfonyl-pyrrolidine-2-carbonyl)-amino]-3-(3-benzyl-ureido)-propionic acid;

or a stereoisomer, partial stereoisomer, pharmaceutically acceptable salt, acid hydrate, or N-oxide thereof.

16. A method for treating at least one integrin α2β1-affected disease state or infection comprising the step of administering to a subject in need thereof a composition comprising a therapeutically effective amount of a compound having the formula:

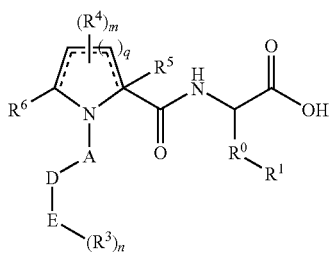

wherein:
R⁰ is methylene;
R¹ is NH(aralkyl), NHSO₂aryl, NHSO₂alkyl, CH₂C(=O) alkoxy, NHSO₂R², or NHC(=O)R²;
R² is aryl, alkyl, alkoxy, aralkyl, aralkoxy, aralkylamino, arylamino, or alkylamino;
Each R³ is independently halo, nitro, aryl, amino, alkyl, alkoxy, NH-Boc, alkylsulfonyl, NHC(=O)alkyl, NHC(=O)aralkyl, or NHC(=O)arylamino;
Each R⁴ is independently amino, hydroxy, aralkoxy, NH(aryl), or NHC(=O)aryl;
R⁵ is H or alkyl;
R⁶ is H or =O;
A is SO₂, PO₂, or C=O;
D is optional and may be one or more CH₂ groups;
E is aryl or heteroaryl;
n is 0, 1, or 2;
m is 0 or 1;
one of the three dashed-line portions may represent a double bond, and,
q is 0, 1, 2, or 3;
or a stereoisomer, partial stereoisomer, pharmaceutically acceptable salt, acid hydrate, or N-oxide thereof.

17. The method according to claim 16 comprising the step of administering to a subject in need thereof a composition comprising a therapeutically effective amount of a compound having the formula:

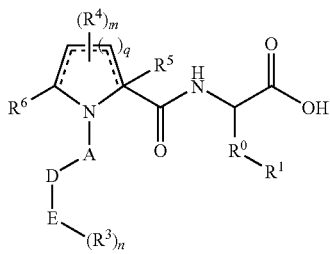

wherein:
R¹ is NH(aralkyl), NHSO₂aryl, CH₂C(=O)alkoxy, or NHC(=O)R²;
R² is aryl, aralkyl, alkoxy, aralkoxy, aralkylamino, arylamino, or alkylamino;
Each R⁴ is independently hydroxy or aralkoxy;
A is SO₂ or C=O; and,
E is aryl;
or a stereoisomer, partial stereoisomer, pharmaceutically acceptable salt, acid hydrate, or N-oxide thereof.

18. The method according to claim 16 wherein the subject is administered a therapeutically effective amount of:

3-tert-Butoxycarbonylamino-2-{[1-(4-nitro-benzenesulfonyl)-pyrrolidine-2-carbonyl]-amino}-propionic acid;

3-Benzyloxycarbonylamino-2-{[1-(4-nitro-benzenesulfonyl)-pyrrolidine-2-carbonyl]-amino}-propionic acid;

3-Benzoylamino-2-{[1-(4-nitro-benzenesulfonyl)-pyrrolidine-2-carbonyl]-amino}-propionic acid;

2-{[1-(4-Nitro-benzenesulfonyl)-pyrrolidine-2-carbonyl]-amino}-3-(3-phenyl-propionylamino)-propionic acid;

3-(3-Benzyl-ureido)-2-{[1-(4-nitro-benzenesulfonyl)-pyrrolidine-2-carbonyl]-amino}-propionic acid;

2-{[1-(4-Nitro-benzenesulfonyl)-pyrrolidine-2-carbonyl]-amino}-pentanedioic acid 5-tert-butyl ester;

3-[3-(2-Chloro-benzyl)-ureido]-2-{[1-(4-nitro-benzenesulfonyl)-pyrrolidine-2-carbonyl]-amino}-propionic acid;

3-[3-(4-Bromo-benzyl)-ureido]-2-{[1-(4-nitro-benzenesulfonyl)-pyrrolidine-2-carbonyl]-amino}-propionic acid;

2-{[1-(4-Nitro-benzenesulfonyl)-pyrrolidine-2-carbonyl]-amino}-3-(3-phenyl-ureido)-propionic acid;

2-{[1-(4-Nitro-benzenesulfonyl)-pyrrolidine-2-carbonyl]-amino}-3-[3-(4-nitro-phenyl)-ureido]-propionic acid;

3-(3-Biphenyl-4-yl-ureido)-2-{[1-(4-nitro-benzenesulfonyl)-pyrrolidine-2-carbonyl]-amino}-propionic acid;

3-[3-(4-Methoxy-benzyl)-ureido]-2-{[1-(4-nitro-benzenesulfonyl)-pyrrolidine-2-carbonyl]-amino}-propionic acid;

3-[3-(2-Methoxy-benzyl)-ureido]-2-{[1-(4-nitro-benzenesulfonyl)-pyrrolidine-2-carbonyl]-amino}-propionic acid;

3-[3-(3-Methoxy-benzyl)-ureido]-2-{[1-(4-nitro-benzenesulfonyl)-pyrrolidine-2-carbonyl]-amino}-propionic acid;

3-(3-Biphenyl-4-ylmethyl-ureido)-2-{[1-(4-nitro-benzenesulfonyl)-pyrrolidine-2-carbonyl]-amino}-propionic acid;

2-{[1-(4-Nitro-benzenesulfonyl)-pyrrolidine-2-carbonyl]-amino}-3-(3-propyl-ureido)-propionic acid;

3-(3-tert-Butyl-ureido)-2-{[1-(4-nitro-benzenesulfonyl)-pyrrolidine-2-carbonyl]-amino}-propionic acid;

3-[3-(4-tert-Butoxycarbonylamino-benzyl)-ureido]-2-{[1-(4-nitro-benzenesulfonyl)-pyrrolidine-2-carbonyl]-amino}-propionic acid;

3-[3-(4-Amino-benzyl)-ureido]-2-{[1-(4-nitro-benzenesulfonyl)-pyrrolidine-2-carbonyl]-amino}-propionic acid;

2-[(1-Benzenesulfonyl-pyrrolidine-2-carbonyl)-amino]-3-(3-benzyl-ureido)-propionic acid;

2-{[1-(4-Acetylamino-benzenesulfonyl)-pyrrolidine-2-carbonyl]-amino}-3-(3-benzyl-ureido)-propionic acid;

3-(3-Benzyl-ureido)-2-[(1-phenylmethanesulfonyl-pyrrolidine-2-carbonyl)-amino]-propionic acid;

2-[2-(3-Benzyl-ureido)-1-carboxy-ethylcarbamoyl]-pyrrolidine-1-carboxylic acid benzyl ester;

3-(3-Benzyl-ureido)-2-{[1-(biphenyl-4-sulfonyl)-pyrrolidine-2-carbonyl]-amino}-propionic acid;

2-{[1-(4-Amino-benzenesulfonyl)-pyrrolidine-2-carbonyl]-amino}-3-(3-benzyl-ureido)-propionic acid;

2-[(1-Benzoyl-pyrrolidine-2-carbonyl)-amino]-3-(3-benzyl-ureido)-propionic acid;

3-(3-Benzyl-ureido)-2-{[1-(toluene-4-sulfonyl)-pyrrolidine-2-carbonyl]-amino}-propionic acid;

3-(3-Benzyl-ureido)-2-{[1-(naphthalene-1-sulfonyl)-pyrrolidine-2-carbonyl]-amino}-propionic acid;

3-(3-Benzyl-ureido)-2-{[1-(naphthalene-2-sulfonyl)-pyrrolidine-2-carbonyl]-amino}-propionic acid;

3-[3-(4-Amino-benzyl)-ureido]-2-[(1-benzenesulfonyl-pyrrolidine-2-carbonyl)-amino]-propionic acid;

3-(3-Benzyl-ureido)-2-{[1-(3,5-dimethyl-benzenesulfonyl)-pyrrolidine-2-carbonyl]-amino}-propionic acid;

3-(3-Benzyl-ureido)-2-{[1-(4-phenylacetylamino-benzenesulfonyl)-pyrrolidine-2-carbonyl]-amino}-propionic acid;

3-(3-Benzyl-ureido)-2-({1-[4-(3-phenyl-ureido)-benzenesulfonyl]-pyrrolidine-2-carbonyl}-amino)-propionic acid;

3-(3-Benzyl-ureido)-2-{[1-(naphthalene-2-sulfonyl)-pyrrolidine-2-carbonyl]-amino}-propionic acid;

2-[(1-Benzenesulfonyl-pyrrolidine-2-carbonyl)-amino]-3-[3-(2-chloro-benzyl)-ureido]-propionic acid;

2-[(1-Benzenesulfonyl-pyrrolidine-2-carbonyl)-amino]-3-(3-phenyl-ureido)-propionic acid;

2-[(1-Benzenesulfonyl-pyrrolidine-2-carbonyl)-amino]-3-(3-phenyl-propionylamino)-propionic acid;

2-[(1-Benzenesulfonyl-pyrrolidine-2-carbonyl)-amino]-3-benzoylamino-propionic acid;

2-[(1-Benzenesulfonyl-pyrrolidine-2-carbonyl)-amino]-3-benzyloxycarbonylamino-propionic acid;

2-[(1-Benzenesulfonyl-pyrrolidine-2-carbonyl)-amino]-3-[3-(2-methoxy-benzyl)-ureido]-propionic acid;

2-[(1-Benzenesulfonyl-pyrrolidine-2-carbonyl)-amino]-3-[3-(3-methoxy-benzyl)-ureido]-propionic acid;

2-[(1-Benzenesulfonyl-pyrrolidine-2-carbonyl)-amino]-3-(3-propyl-ureido)-propionic acid;

3-(3-Benzyl-ureido)-2-{[1-(3,5-difluoro-benzenesulfonyl)-pyrrolidine-2-carbonyl]-amino}-propionic acid;

3-(3-Benzyl-ureido)-2-{[1-(4-methanesulfonyl-benzenesulfonyl)-pyrrolidine-2-carbonyl]-amino}-propionic acid;

2-[(1-Benzenesulfonyl-pyrrolidine-2-carbonyl)-amino]-3-(3-tert-butyl-ureido)-propionic acid;

2-[(1-Benzenesulfonyl-4-benzyloxy-pyrrolidine-2-carbonyl)-amino]-3-(3-benzyl-ureido)-propionic acid;

2-[(1-Benzenesulfonyl-4-hydroxy-pyrrolidine-2-carbonyl)-amino]-3-(3-benzyl-ureido)-propionic acid;

3-(3-Benzyl-ureido)-2-{[1-(3,5-dichloro-benzenesulfonyl)-pyrrolidine-2-carbonyl]-amino}-propionic acid;

3-(3-Benzyl-ureido)-2-{[1-(3,5-bis-trifluoromethyl-benzenesulfonyl)-pyrrolidine-2-carbonyl]-amino}-propionic acid;

2-[(1-Benzenesulfonyl-piperidine-2-carbonyl)-amino]-3-(3-benzyl-ureido)-propionic acid;

2-[(1-Benzenesulfonyl-2,5-dihydro-1H-pyrrole-2-carbonyl)-amino]-3-(3-benzyl-ureido)-propionic acid; or, 2-[(1-Benzenesulfonyl-pyrrolidine-2-carbonyl)-amino]-3-(3-benzyl-ureido)-propionic acid;

or a stereoisomer, partial stereoisomer, pharmaceutically acceptable salt, acid hydrate, or N-oxide thereof.

19. The method according to claim 16, wherein the disease state or infection is vascular, cancer-related, diabetes-related, or rheumatoid.

20. The method according to claim 16 wherein the subject is suffering from or susceptible to one or more of acute coronary syndromes, stroke, ischaemic complications of peripheral vascular disease, deep vein thrombosis (DVT), myocardial infarction, coronary artery disease, cerebrovascular disease, peripheral arterial disease, diabetes mellitus, atrial fibrillation, congestive heart failure, pulmonary embolism, and other vascular-related disorders.

21. The method according to claim 16, wherein the subject is suffering from or susceptible to one or more of human melanoma, hepatocellular carcinoma, breast cancer, lung cancer, ovarian cancer, and other cancers or cancer-related disorders.

22. The method according to claim 16, wherein the subject is suffering from or susceptible to one or more of rheumatoid arthritis, diabetic retinopathy, and other rheumatoid- or diabetes-related disorders.

23. The method according to claim 16, wherein the disease state or infection is matrix reorganization-affected.

24. The method according to claim 16, wherein the disease state or infection is angiogenesis-affected.

25. The method according to claim 16, wherein the disease state or infection is cell migration-, cell proliferation-, cell colonization-, or metastasis-affected.

26. The method according to claim 16, wherein the disease state or infection is leukocyte infiltration-affected.

27. The method according to claim 16, wherein the disease state or infection is edema-affected.

28. The method according to claim 16, wherein the subject is suffering from or susceptible to viral infection.

29. The method according to claim 16, wherein said viral infection is at least partially attributable to human cytomegalovirus (HCMV), rotaviruses, Piconaviridae viruses, or related viruses.

30. The method according to claim 16 wherein said composition additionally comprises a pharmaceutically acceptable carrier, diluent, or excipient.

31. The method according to claim 16, wherein said composition comprises a stereochemically enriched mixture of compounds of the formula.

32. The method according to claim 16, wherein said subject is human.

33. The method according to claim 16, where said subject is a non-human animal.

* * * * *